(12) United States Patent
Temple et al.

(10) Patent No.: US 10,034,916 B2
(45) Date of Patent: Jul. 31, 2018

(54) METHODS OF TREATING A RETINAL DISEASE BY RETINAL PIGMENT EPITHELIAL STEM CELLS

(71) Applicant: REGENERATIVE RESEARCH FOUNDATION, Rensselaer, NY (US)

(72) Inventors: Sally Temple, Slingerlands, NY (US); Jeffrey Stern, Slingerlands, NY (US); Enrique L. Salero-Coca, Delmar, NY (US)

(73) Assignee: Regenerative Research Foundation, Rensselaer, NY (US)

( * ) Notice: Subject to any disclaimer, the term of this patent is extended or adjusted under 35 U.S.C. 154(b) by 0 days.

(21) Appl. No.: 13/915,845

(22) Filed: Jun. 12, 2013

(65) Prior Publication Data

US 2013/0330302 A1    Dec. 12, 2013

Related U.S. Application Data

(63) Continuation of application No. 12/428,456, filed on Apr. 22, 2009, now Pat. No. 8,481,313.

(60) Provisional application No. 61/047,102, filed on Apr. 22, 2008.

(51) Int. Cl.
| | |
|---|---|
| A61K 48/00 | (2006.01) |
| C12N 5/0797 | (2010.01) |
| C12N 5/0735 | (2010.01) |
| C12N 5/074 | (2010.01) |
| C12N 5/0793 | (2010.01) |
| C12N 5/071 | (2010.01) |
| C12N 5/07 | (2010.01) |
| C12N 5/16 | (2006.01) |
| G01N 33/567 | (2006.01) |
| A01N 1/00 | (2006.01) |
| A01N 63/00 | (2006.01) |
| A61K 38/18 | (2006.01) |
| C12N 5/079 | (2010.01) |

(52) U.S. Cl.
CPC ........ *A61K 38/1825* (2013.01); *C12N 5/0607* (2013.01); *C12N 5/0619* (2013.01); *C12N 5/0621* (2013.01); *C12N 2501/115* (2013.01); *C12N 2501/119* (2013.01); *C12N 2501/385* (2013.01); *C12N 2501/41* (2013.01); *C12N 2506/02* (2013.01); *C12N 2506/08* (2013.01); *C12N 2533/52* (2013.01)

(58) Field of Classification Search
CPC ............ C12N 5/0621; C12N 2501/115; C12N 5/0623; C12N 2501/11; C12N 2501/41; C12N 5/0607; C12N 5/06; C12N 5/0618; C12N 2506/02; C12N 2506/08; A61K 35/12; A61K 35/545; A61K 38/0038; A61K 38/1825; A61K 38/185; A61K 9/0051; A61L 2300/64; G01N 33/5044; G01N 33/5058; G01N 33/5073; A61F 2/14

See application file for complete search history.

(56) References Cited

U.S. PATENT DOCUMENTS

| | | | | |
|---|---|---|---|---|
| 6,117,675 | A * | 9/2000 | van der Kooy et al. | 435/354 |
| 6,299,895 | B1 * | 10/2001 | Hammang et al. | 424/427 |
| 6,436,427 | B1 * | 8/2002 | Hammang et al. | 424/427 |
| 6,649,184 | B2 * | 11/2003 | Hammang et al. | 424/427 |
| 7,514,259 | B2 * | 4/2009 | Young et al. | 435/366 |
| 7,736,896 | B2 * | 6/2010 | Klimanskaya | A61K 35/44 435/325 |
| 7,794,704 | B2 * | 9/2010 | Klimanskaya | A61K 35/12 424/93.7 |
| 7,795,025 | B2 * | 9/2010 | Klimanskaya | 435/325 |
| 8,268,303 | B2 * | 9/2012 | Klimanskaya | A61K 35/12 424/93.7 |
| 8,900,567 | B2 * | 12/2014 | Friedlander | C12N 5/0647 424/93.21 |
| 9,005,965 | B2 * | 4/2015 | Shushan | C12N 5/0606 435/325 |
| 9,040,038 | B2 * | 5/2015 | Klimanskaya | A61K 35/12 424/93.7 |
| 9,040,039 | B2 * | 5/2015 | Klimanskaya | A61K 35/12 424/93.7 |
| 9,040,770 | B2 * | 5/2015 | Klimanskaya | A61K 35/44 800/3 |
| 9,045,732 | B2 * | 6/2015 | Klimanskaya | A61K 35/12 |

(Continued)

FOREIGN PATENT DOCUMENTS

| | | |
|---|---|---|
| WO | 2001/058460 | 8/2001 |
| WO | 2005/021720 | 3/2005 |

OTHER PUBLICATIONS

Julien et al. "Tyrosinase biosynthesis and traficking in adult human retinal pigment epithelial cells", Graefe's Arch. Clin. Exp. Ophthalmol (2007) 245:1495-1505.

(Continued)

*Primary Examiner* — Chang-Yu Wang
(74) *Attorney, Agent, or Firm* — Fish & Richardson P.C.

(57) ABSTRACT

The present invention relates to a retinal pigment epithelial stem cell isolated from a posterior region of the retinal pigment epithelium of an adult mammal. The invention also relates to a method of inducing differentiation of retinal epithelial stem and progenitor cells in vitro, wherein the cells of the invention are highly plastic, multipotential stem cells. The invention also includes methods for the treatment of retinal diseases and vision loss involving the transplantation of retinal pigment epithelial stem cells or cells differentiated from retinal pigment epithelial stem cells to the retina of a patient in need of treatment.

12 Claims, 4 Drawing Sheets

(56) References Cited

U.S. PATENT DOCUMENTS

| | | | | |
|---|---|---|---|---|
| 9,080,150 | B2* | 7/2015 | Klimanskaya | A61K 35/12 |
| 9,181,524 | B2* | 11/2015 | Klimanskaya | A61K 35/12 |
| 9,193,950 | B2* | 11/2015 | Klimanskaya | A61K 35/12 |
| 2002/0061327 | A1* | 5/2002 | Hammang et al. | 424/424 |
| 2003/0031700 | A1* | 2/2003 | Hammang et al. | 424/424 |
| 2006/0018886 | A1* | 1/2006 | Klimanskaya | A61K 35/44 424/93.7 |
| 2006/0031951 | A1* | 2/2006 | Klimanskaya | A61K 35/12 800/14 |
| 2006/0104963 | A1* | 5/2006 | Friedlander | C12N 5/0692 424/93.21 |
| 2007/0031386 | A1* | 2/2007 | Klimanskaya | A61K 35/44 424/93.7 |
| 2007/0196919 | A1* | 8/2007 | Reh et al. | 435/368 |
| 2007/0231310 | A1* | 10/2007 | Friedlander | C12N 5/0647 424/93.21 |
| 2008/0317721 | A1* | 12/2008 | Friedlander | A61K 31/137 424/93.21 |
| 2009/0104695 | A1* | 4/2009 | Shushan | C12N 5/0606 435/366 |
| 2009/0170148 | A1 | 7/2009 | Smirnova | |
| 2010/0021422 | A1 | 1/2010 | Temple | |
| 2010/0299765 | A1* | 11/2010 | Klimanskaya | A61K 35/44 800/3 |
| 2011/0117062 | A1* | 5/2011 | Klimanskaya | A61K 35/44 424/93.7 |
| 2011/0117063 | A1* | 5/2011 | Klimanskaya | A61K 35/12 424/93.7 |
| 2011/0177594 | A1* | 7/2011 | Shushan | C12N 5/0606 435/366 |
| 2011/0274662 | A1* | 11/2011 | Malcuit et al. | 424/93.7 |
| 2013/0022680 | A1* | 1/2013 | Klimanskaya | A61K 35/12 424/490 |
| 2013/0302286 | A1* | 11/2013 | Klimanskaya | A61K 35/12 424/93.7 |
| 2013/0302288 | A1* | 11/2013 | Klimanskaya | A61K 35/12 424/93.7 |
| 2013/0302426 | A1* | 11/2013 | Klimanskaya | A61K 35/12 424/490 |
| 2013/0316451 | A1* | 11/2013 | Klimanskaya | A61K 35/12 435/366 |
| 2013/0316452 | A1* | 11/2013 | Klimanskaya | A61K 35/12 435/371 |
| 2014/0294779 | A1* | 10/2014 | Klimanskaya | A61K 35/12 424/93.7 |
| 2014/0356432 | A1* | 12/2014 | Klimanskaya | A61K 35/12 424/484 |
| 2015/0250828 | A1* | 9/2015 | Kamao | A61K 35/44 435/377 |
| 2015/0328261 | A1* | 11/2015 | Klimanskaya | A61K 35/44 424/93.7 |

OTHER PUBLICATIONS

Forman et al. "Neurodegenerative diseases: a decade of discoveries paves the way for therapeutic breakthroughs", Nat Med. (2004), vol. 10:1055-1063.
Drvja et al. "Demonstration of tyrosinase in the adult bovine uveal tract and retinal pigment epithelium", (1978) Invest. Ophthalmol. Vis. Sci 17:511-514.
Smith et al. Expression of tyrosinase and the tyrosinase related proteins in the Mitf (Vitiligo) mouse eye: implications for the function of the microphthalmia transcription factor (Mitf), (1998) Exp. Eye. Res. 66:403-410.
Perrier at al. "Derivation of midbrain dopamine neurons from human embryonic sternm cells", (2004) Proc. Natl. Acad. Sci. USA 101:12543-12548.
Auerbach et al. "Tumor-induced angiogenesis: lack of inhibition by irradiation", Int. J. Cancer (1975) 15:241-245.
Leng et al. "The chick chorioallantoic membrane as a model tissue for surgical retinal research and simulation", 2004 24: (3):427-434.
De et al. "Human retinal pigment epithelium cell changes and express of αB-Crystallin", Arch Opthalmol. (2007) 125:641-646.
Park. et al. "Reprogramming of human somatic cells to pluripotency with defined factors", Nature (2008) 451:141-146.
Nakagawa et al. "Generation of induced pluripotent stem eells without Myc from mouse and human fibroblasts", Nature Biotechnol. (2008) 26:101-106.
Yu et al. "Induced pluripotent stem cell lines derived from human somatic cells", Science (2007) 318:1917-1920.
Shen et al. "Endothelial cells stimulate self-renewal and expand neurogenesis of neural stem cells" Science: 304:1338-1340 (2004).
Wurmser et al. "Cellular interactions in the stem cell niche", Science, 304:1253-1255 (2004).
Da Cruz et al., "RPE transplantation and its role in retinal disease", Scence Direct (2007) Progress in Retinal and Eye Research 26:598-635.
Dunn et al., "ARPE-19 a human retinal pigment epithelial cell line With differentiated properties" Exp. Eye Res. (1996) 62:155-169.
Gu et al. Isolation of retinal progenitor and stem cells from the porcine eye. IN: Mol Vis Jun. 29, 2007, 13(1): 1045-1057. Especially abstract, p. 1049 right col para 2.
Alge et al. "Retinal pigment epithelium is protected against apoptosis by alphaB-crystallin" Invest Ophthalmol Vis Sci. Nov. 2002:43(11):3575-82; especially abstract.
Setoguchi, T. et al. "Nuclear export of OLIG2 in neural stem cells is essential for ciliary neurotrophic factor-induced astrocyte differentiation," (2004) 1. Cell Bioi.; 166:963-968.
Orger, M. et al. "Control of visually guided behavior by distinct populations of spinal projection neurons," Neurosci. 2008 11(3):327-333.
Poche, R. et al. "Lim1 is essential or the correct laminar positioning of retinal horizontal cells," J Neuroscience (2007) 27(51):14099-14107.
Nickerson, P. et al. "Proliferation and expression of progenitor and mature retinal phenotypes in the adult mammalian ciliary body after retinal ganglion cell injury" Investigative Ophthalmology & Visual Science, 48(11):5266-5275 (2007).
Das, A. V. et al. "Retinal properties and potential of the adult mammalian ciliary epithelium stem cells" Vision Research, 45(13):1653-1666 (2005).
Stem, J. and Temple S. "Stem cell or retinal replacement therapy" Neurotherapeutics, 8(4):736-743 (2011).
Salero, E. et al. "Adult human RPE can he activated into a multipotent stem cell that produces mesenchymal derivatives" Cell Stem Cell, 10(1):88-95 (2012).
Gu, P. el al. "Isolation of retinal progenitor and stem cells from the porcine eye" Molecular Vision, 13:1045-1057(2007) Especially abstract, p. 1049 right col para 2.
European Extended Search Report received in co-pending European Application No. 09734972.4 dated Jul. 31, 2012—8 pages.
Reh & Fischer Methods Enzymol (2006) 419:52-73.
Bharti et al., Pigment Cell Res. (2006) 19(5):380-394.
Park & Hollenberg, Dev. Biol. (1989) 134:201-205.
Sakaguchi et al. Dev. Dyn. (1997) 209(4):387-398.
Ma et al. Dev. Biol. (2004) 265(2):320-328.
Azuma et al. Mol. Genet, (2005) 14(8): 1059-1068.
Yan & Wang, Neurosci. Lett. (2000) 280(2):83-86.
Machemer & Laqua, Am. J. Qphthalmol (1975) 80:1-23.
Amemiya et al. Biochem. Biophys. Res. Commun. (2004) 316:1-5.
Vinores et al., Exp. Eye Res. (1995) 60:385-400.
Ohta et al. Dev. Growth Differ. (2008) 50:253-259.
Tropepe et al. Science (2000) 287:2032-2036.
Cicero et al. Proc. Nat. Acad. Sci U.S.A.(E-publication Apr. 3, 2009); 106(16):6685-6690.
Haruta et al. Invest Ophtlalmol. Vis. Sci. (2004) 45:1020-1025.
Lund et al. Cloning Stem Cells (2006) 8:189-199.
Klimanskaya et al. Cloning Stem Cells (2004) 6:217-245.
Ando et al. (2007) J. Invest Dermatol. 127:751-761.
Bloom et al., Annals of Medicine 109(12): 963-968 (1988).
Anglade et al. Drugs, 49(2):213-223 (1995).
Penfold et al. (2001) Prog. Retinal Eye Res. 20, 385-414.
Sarks and Sarks (1994) Chapter 67 in Retina, vol. 2, ed. S. Ryan. Publ. Mosby.

(56) References Cited

OTHER PUBLICATIONS

Ciulila et al. (1998) Surv. Ophthalmol. 43, 134-146.
Forman et al. (2004) Nat. Med. 10:1055-1063.
Homykiewicz et al. (2001) J. Chem. Neuroanat 22:3-12.
Calne et al. (1992) Ann. Neurol. 32 Suppl:S125-127.
Nikoskelainen et al. (1995) J. Neurol. Neurosurg. Psychiatry 2:160-164.
Hoegger et al. (2008) BMC Neurosci 8;9:4.
Reeck et al. Cell 1987; 50:667.
Burke et al. Exp. Eye Res. (1996) 62:63-73.
Maminiskhis et al. Invest. Ophthalmol. Vis. Sci. (2006) 47:3612-3624.
Duplomb et al. Stem Cells. Mar. 2007;25(3):544-52.
Kamer et al. Stem Cells Dev. (2007) 16:39-52.
Hosseinkhani et al. Stem Cells (2007) 25:571-580.
Yao et al. Proc. Natl. Acad. Sci. U.S.A. (2006) 103:6907-6912.
Gouon-Evans et al. Nat. Blotechnol. (2006) 24:1402-1411.
Kubo et al. Development (2004) 131:1651-1662.
De et al. Arch. Ophthalrnol (2007) 125:641-645.
Reynolds & Rietze Nat. Methods (2005) 2:333-336.
Martinez-Morales et al. Bioessays (2004) 26:766-777.
Ohno-Matsui et al. Mol. Vis. (2005) 1:1-1 0.
Wang et al. Nature (2006) 444:364-368.
Carpenter et al. Cloning Stem Cells (2003) 5:79-88.
Avilion et al. Genes and Development 2003 17(1) 136-140.
Hever et al. Clin. Genet. (2006) 69:459-470.
Takahashi et al. Cell (2007) 131:861-872.
Maherali et al. Cell Stem Cell (2007) 1:55-70.
Osakada et al. Nat. Biotechnol. (2008) 26:215-224.
Trounson, Endocrine Reviews (2006) 27:208-219.
Lu et al. (2007) Mol. Vis. 13:2066-2072.
Angeletti, R. H., and Bradshaw, R. A. Nerve growth factor from mouse submaxillary gland: amino acid sequence. Proc. Natl. Acad. Sci. U. S. A. 1971 68, 2417-2420.
Levi-Montalcini et al., Differentiating effects of murine nerve growth factor in the peripheral and central nervous systems of Xenopus laevis tadpoles, Proc Natl Acad Sci USA. Oct. 1985; 82(20):7111-5).
Eveleth, DD, Cell-based therapies for ocular disease, J Ocul Pharmacol Ther. Dec. 2013;29(10):844-54).

* cited by examiner

METHODS OF TREATING A RETINAL DISEASE BY RETINAL PIGMENT EPITHELIAL STEM CELLS

CROSS-REFERENCE TO RELATED APPLICATIONS

This is a continuation of prior U.S. application Ser. No. 12/428,456, which was filed on Apr. 22, 2009 and issued, on Jul. 9, 2013, as U.S. Pat. No. 8,481,313. Said U.S. application Ser. No. 12/428,456 claims priority to U.S. provisional application Ser. No. 61/047,102 filed Apr. 22, 2008, the contents of which are hereby incorporated by reference in their entirety.

STATEMENT REGARDING GOVERNMENT SPONSORED RESEARCH OR DEVELOPMENT

This invention was made in part in the course of research sponsored by the Ruth and Milton Steinbach Fund, Inc. This entity may have certain rights in this invention.

FIELD OF THE INVENTION

The present invention relates to retinal pigment epithelial stem cells (RPESCs), isolated from the retinal pigment epithelium (RPE) of adult mammals, which may be differentiated into a wide variety of progeny from each of the major developmental, lineages. The invention also includes pharmaceuticals made with RPESCs or retinal cells which may be used to restore vision lost due to diseases, disorders or abnormal physical states of the retina, other neurological, non-neurological diseases, such as cancer, and/or tissues injuries that benefit from stem cell replacement therapy.

BACKGROUND OF THE INVENTION

The therapeutic strategies for treating loss of vision caused by retinal cell damage vary, but they are all directed to controlling the illness causing the damage, rather than reversing the damage caused by an illness by restoring or regenerating retinal cells. As one example, the treatments of uveitis are drawn from the knowledge of changes in the retinal environment when inflammation occurs. Corticosteroids, such as prednisone, are the preferred drug of treatment. However, these drugs are immunosuppressants with numerous side effects. As well, the systemic immunosuppression may have significant negative effects on the development of children as well as on adults in poor health, such as the elderly and patients with chronic disease. These patients must try alternative drugs such as alkylating agents or antimetabolites, which also have side effects. Clearly, patients with eye diseases remain vulnerable to sustaining permanent damage to the retinal cells, even if drug treatments are available. Thus, successful treatments of retinal cell damage will include approaches that aid in the regeneration of damaged retinal cells without causing the harmful side effects caused by current treatment methods.

A current area of study that will be important for treating diseases of the eye and other tissues involves the use of stem cells to regenerate damaged cells. Stem cells are undifferentiated cells that exist in many tissues of embryos and adult mammals. In embryos, blastocyst stem cells are the source of cells which differentiate to form the specialized tissues and organs of the developing fetus. In adults, specialized stem cells in individual tissues are the source of new cells which replace cells lost through cell death due to natural attrition, disease or injury. No stem cell is common to all tissues in adults. Rather, the term "stem cell" in adults describes different groups of cells in different tissues and organs with common characteristics.

Stem cells are capable of producing either new stem cells or cells called progenitor cells that differentiate to produce the specialized cells found in mammalian organs. Symmetric division occurs where one stem cell divides into two daughter stem cells. Asymmetric division occurs where one stem cell forms one new stem cell and one progenitor cell. A progenitor cell differentiates to produce the mature specialized cells of mammalian organs. In contrast, stem cells never terminally differentiate (i.e., they never differentiate into a specialized tissue cell). Progenitor cells and stem cells are referred to collectively as "precursor cells". This term is used when it is unclear whether a researcher is dealing with stem cells or progenitor cells or both.

Progenitor cells may differentiate in a manner which is unipotential or multipotential. A unipotential progenitor cell is one which can form only one particular type of cell when it is terminally differentiated. A multipotential progenitor cell has the potential to differentiate to form more than one type of tissue cell. Which type of cell it ultimately becomes depends on conditions in the local environment such as the presence or absence of particular peptide growth factors, cell-cell communication, amino acids and steroids. For example, it has been determined that the hematopoietic stem cells of the bone marrow produce all of the mature lymphocytes and erythrocytes present in fetuses and adult mammals. There are several well-studied progenitor cells produced by these stem cells, including three unipotential and one multipotential tissue cell. The multipotential progenitor cell may divide to form one of several types of differentiated cells depending on which hormones act upon it.

FIG. 1 shows a schematic cross-section of the human eye, in which both the retina and the retinal pigment epithelium (RPE) are indicated. The retina is a layer of light sensitive tissue lining the inner surface of the eye. The RPE is a layer of pigmented cells just beneath the retina, which nourishes and supports the overlying retinal cells.

Retinal progenitor cells (RPCs) are multipotent, proliferative, and give rise to the various retinal cell types, while retinal pigment epithelium (RPE) progenitor cells normally generate solely RPE. Reh & Fischer, *Methods Enzymol.* (2006) 419:52-73. The RPE is a monolayer of neuroepithelial cells underlying and supporting the sensory retina. During development the RPE begins as a plastic tissue capable of regenerating lens or sensory retina but then differentiates very early [around E38 in humans and E9.5 in mouse (Bharti et al., *Pigment Cell Res.* (2006) 19(5):380-394)] and remains non-proliferative throughout life. RPE cells form a pigmented, single cell epithelium between the neural retina and the vascular choriocapillaris that has important roles in maintaining photoreceptor function. During development, the optic neuroepithelium evaginates into two outpocketings of the diencephalon. The dorsal aspect of the resulting optic vesicle is specified to generate the RPE, while the ventral aspect becomes neural retina. Bharti et al., *Pigment Cell Res.* (2006) 19(5):380-394. The other types of cells located in the retina include rod cells, cone cells, bipolar cells, amacrine cells, horizontal cells, Müller cells, glial cells, and retinal ganglion cells.

Interestingly, in amphibians, and in embryonic chick, RPE cells can produce other retinal and even lens tissues, indicating an inherent plasticity. Reh & Fischer, *Methods Enzymol.* (2006) 419:52-73. In amphibians, embryonic chick and embryonic rodents, RPE cells can proliferate and differentiate into neural progenitors and retinal cells. Id. This can occur in vivo and in vitro after induction with fibroblast growth factors (FGFs) (Park & Hollenberg, *Dev. Biol.* (1989) 134:201-205; Sakaguchi et al., *Dev. Dyn.* (1997) 209(4):387-398), or after enforced expression of retinal development genes, including Pax6, Ath5, NeuroD and NSCL, or after surgical removal of endogenous neural retina. Ma et al., *Dev. Biol.* (2004) 265(2):320-328; Azuma et al., *Mol. Genet.* (2005) 14(8):1059-1068; Yan & Wang, *Neurosci. Lett.* (2000) 280(2):83-86. In humans, RPE cells can proliferate in vivo, for example following retinal detachment (Machemer & Laqua, *Am. J. Ophthalmol.* (1975) 80:1-23) and in vitro they proliferate and differentiate into β-tubulin III$^+$ neurons, but their capacity to differentiate into a variety of neural cell types has not been demonstrated. Amemiya et al., *Biochem. Biophys. Res. Commun.* (2004) 316:1-5; Vinores et al., *Exp. Eye Res.* (1995) 60:385-400.

Retinal stem cells (RSCs) isolated from the ciliary epithelium and iris pigmented epithelium of adult rodents and humans have been described, and are reported to self-renew in vitro and differentiate into retinal neurons and glia. Reh & Fischer, *Methods Enzymol.* (2006) 419:52-73; Ohta et al., *Dev. Growth Differ.* (2008) 50:253-259. See also U.S. Pat. No. 6,117,675; and Tropepe et al., *Science* (2000) 287:2032-2036. However, these reports have been criticized by others, who have presented data indicating that the putative RSCs are, in fact, differentiated, pigmented ciliary epithelial cells. See Cicero et al., "Cells Previously Identified as Retinal Stem Cells Are Pigmented Ciliary Epithelial Cells," *Proc. Nat. Acad. Sci. U.S.A.* (e-publication Apr. 3, 2009) <URL http://www.pnas.org/cgi/doi/10.1073/pnas.0901596106> (last accessed Apr. 13, 2009). Moreover, there is as yet no evidence that a stem-like cell exists in the adult RPE. It is particularly important to look for the presence of these cells in humans, because of the relevance to human ocular diseases such as retinitis pigmentosa (RP), cone dystrophy, and age-related macular degeneration. da Cruz et al., *Prog. Retin. Eye Res.* (2007) 26:598-635.

There are no known successful treatments for RP and other retinal dystrophies. There are also no treatments which regenerate new cells endogenously or which transplant healthy tissue to the retina. Even if it were possible to develop some form of transplantation, it would be subject to the same problems that accompany transplants in other organ systems. These include: in many cases, implants provide only temporary relief as the symptoms associated with the disease often return after a number of years, rejection by the patient of foreign tissue, adverse reactions associated with immunosuppression (immunosuppression is needed to try to help the patient accept the foreign tissue), the inability of a sufficient number of cells in the tissue being implanted to survive during and after implantation, transmitting other diseases or disorders may be transmitted to the patient via the implant, and the results may not justify the costs and efforts of a complex procedure.

Thus, there is a need for new treatment options, other than transplantation, for the treatment of diseases of the retina and of many other tissues where cell regeneration would be beneficial. Given the immense potential for stem cells to provide new therapeutic treatments for a broad array of human diseases such as those described above, there remains a need for stem and/or progenitor cells that may be easily isolated from adult tissue, and that are multipotential, thereby having the capacity to differentiate into a broad array of different tissue types. The present invention describes such cells.

The citation and/or discussion of cited references in this section and throughout the specification is provided merely to clarify the description of the present invention and is not an admission that any such reference is "prior art" to the present invention. All cited references are incorporated herein by reference in their entirety.

SUMMARY OF THE INVENTION

The present invention provides a type of stem cell that is referred to throughout this specification and the claims as a retinal pigment epithelial stem cell or "RPESC". RPESC of the invention are self-renewing; that is to say, they are capable of replicating (typically through mitotic division) to produce progeny cells that are the same RPSEC cell type. RPESC of the invention can preferably go through a plurality of cell division cycles while maintaining their undifferentiated state; i.e., while maintaining their identity as RPESC. Even more preferably, RPESC of the invention can go through at least six, more preferably at least ten and still more preferably at least 11 or more passages and still maintain their identity as RPESC. In addition, RPESC of the invention are capable of differentiating into any of a plurality of different progeny cell types which, in turn, can give rise to a plurality of different fully differentiated cell types. For example, RPESC of the invention can be differentiated to obtain retinal progenitor cells; retinal neurons and other neuronal cell lines such as dopaminergic neurons (i.e., neuronal cells that synthesize or are capable of synthesizing dopamine) and neural crest cells; as well as other progenitor and differentiated cell lines, including different mesoderm lineages (for example, myogenic, osteogenic, chondrogenic and/or adipogenic lineages), endoderm lineages such as hepatic lineages, and/or ectoderm lineages. The invention therefore includes methods for differentiating RPESC into any of these different cell types or cell lines.

Preferred RPESC of the invention are characterized by the fact that, in addition to being self renewing and capable of differentiating into any of a plurality of different cell types, they are isolated from the retinal pigment epithelium ("RPE") of an animal, which is preferably a mammal and even more preferably a human, or they are derived from (e.g., are descended from or are the progeny of) other cells (typically other RPESC) derived from the such RPE. However, RPESC of the invention can be obtained from other tissues and cell types, and are not limited to RPESC isolated or derived from RPE cells or tissue. For example, it is understood that other stem cells, such as embryonic stem cells ("ESC") from humans and other organisms (preferably other mammals) can be induced to differentiate into RPESC, and such RPESC are also considered part of the invention. For example, it is to be understood that RPESC of the invention may be obtained by culturing a human or other ESC line under conditions described, e.g., by Haruta et al., *Invest. Ophthalmol. Vis. Sci.* (2004) 45:1020-1025; and by Lund et al., *Cloning Stem Cells* (2006) 8:189-199, for differentiating those ESC into retinal cells.

Preferred RPESC of the invention can also be characterized by the presence or absence of certain cellular markers; i.e., the RPESC are said to either express or to not express certain cellular markers. The presence or absence of cellular markers characteristic of RPESC and other cell lines of this invention can be detected using techniques and other procedures that are well known and routine to persons of ordinary skill in the relevant field(s) of this invention. Preferred methods including immuno-detection of proteins corresponding to the different cellular markers in cells or tissue samples of interest, e.g., in a western blot type of analysis, as well as polymerase chain reaction ("PCR") methods such as reverse-transcriptase polymerase chain reaction ("RT-PCR") and quantitative real time polymerase chain reaction ("qPCR" or "qRT-PCR") for detecting the expression of messenger RNA (mRNA) corresponding to the different markers, or cDNA derived therefrom, in cell or tissue samples.

Exemplary methods for practicing these techniques, including preferred antibodies and nucleotide primer for detecting different markers useful to this invention, are described in the examples. Those skilled in the relevant art(s) will recognize, however, that these lists of antibodies and primers are not exclusive, and will be able to readily isolate and/or design other suitable antibodies and/or primers that will be suitable for detecting these markers, including suitable homologs and orthologs of the human genes and proteins listed in this application (e.g., orthologs and homologs isolated from other species of organism, such as from other mammals). Likewise, the detection of cellular markers useful in this invention is not limited to the techniques described in the examples; any techniques suitable for determining whether a particular marker is or is not expressed by a particular cell or tissue sample can be used. A cellular marker is said to be expressed when it is detected in a cell or tissue sample using one of these techniques. Conversely, a particular marker is said to not be expressed if it is not detected, to within the detectable limits of the relevant technique, in a cell or tissue sample.

Preferred RPESC of the invention express or are capable of expressing one or more markers characteristic of RPE cells and/or tissue; and/or they express or are capable of expressing one or more markers characteristic of embryonic stem cells ("ES cells" or "ESC") and/or of induced pluripotent stem cells ("iPSC"). Preferred markers characteristic of RPE cells and tissue include the cellular markers RPE65, Mitf, Cralbp, Otx2 and Bestrophin. Preferred markers characteristic of ESC include the cellular markers SSEA-4, Sox2, KLF4 and c-Myc. Hence, in preferred embodiments, RPESC of the invention express or are capable of expressing one or more markers characteristic of RPE cells and/or tissue, which are preferably selected from the group consisting of RPE65, Mitf, Cralbp, Otx2 and Bestrophin. In other preferred embodiments, an RPESC of the invention expresses or is capable of expressing one or more markers characteristic of an ESC, which are preferably selected from the group consisting of SSEA-4, Sox2, KLF4 and c-Myc. In still other embodiments, an RPESC of the invention expresses or is capable of expressing one or more markers characteristic of RPE cells and/or tissue, and may also express one or more markers characteristic of an ESC, such as any one or more of the markers recited in the different Markush groups, supra.

A particularly preferred marker characteristic of ES cells is Sox2. Hence, in particularly preferred embodiments, an RPESC of the invention expresses or is capable of expressing Sox2.

In preferred embodiments, the RPESC of this invention do not express the cellular marker CHX10. In still other embodiments, an RPESC of the invention may be transformed or transfected with a heterologous gene, e.g., in an expression construct or other suitable expression system.

The present invention also provides methods that use RPESC of the invention to treat various disease and disorders, including retinal diseases and disorders, and neurodegenerative diseases and disorders. Retinal diseases and disorders that may be treated according to the invention include, but are not limited to, macular degeneration, including age-related macular degeneration ("AMD"), retinitis pigmentosa and Leber's hereditary optic neuropathy. A particularly preferred retinal disease for treatment using the methods of this invention is age-related macular degeneration. Preferred methods of treating these and other retinal diseases and disorders comprise the administration, to the retina of a patient, an RPESC according to the invention in an amount effective for treating or ameliorating the retinal disease or disorder. In other preferred methods, an RPESC of the invention is differentiated, preferably in vitro, to obtain retinal cells, which are then administered to the retina of a patient in an amount effective for treating or ameliorating the disease or disorder. In particularly preferred embodiments, the RPESC used in these methods are RPESC isolated from the patient being treated.

A preferred neurodegenerative disease that may be treated according to the invention includes, but is not limited to, Parkinson's disease ("PD"). Preferred methods of treating PD and other neurodegenerative diseases involve administering, to a patient, an RPESC according to the invention in an amount effective for treating or ameliorating the neurodegenerative disease or disorder. In other preferred methods, an RPESC of the invention is differentiated, preferably in vitro, to obtain neural cells, preferably dopaminergic neural cells, which are administered to the patient in an amount effective for treating or ameliorating the disease or disorder. In particularly preferred embodiments, the RPESC used in these methods are RPESC isolated from the patient being treated.

It is to be understood that, in these and other treatment regiments described herein, RPESC can be administered to the patient along with one or more exogenous factors (e.g., one or more growth factors) to induce their differentiation in vivo to a desired cell type. For example, an RPESC of the invention may be isolated from the retina of the patient and propagated in vitro to obtain a number of cells effective for treating the patient. The propagated RPESC can then be administered to the patient along with one or more of the growth factors described in the examples, infra, for differentiating RPESC into a desired cell type (e.g., retinal or neuron cells). One or more other exogenous factors, such as those described in U.S. patent application Ser. No. 12/398,888 filed Mar. 5, 2009 and incorporated herein by reference in its entirety can also be administered in combination with RPESC of the invention. Growth and other exogenous factors can also be administered, e.g., by administering one or more cells that secrete the factors into the eye, such as genetically engineered cells carrying a vector that expresses a desired factor, coupled to a suitable promoter and secretion signal It is to be understood that references to administering RPESC "in combination" with one or more other elements (e.g., growth or exogenous factors) includes, unless otherwise indicated, administering other elements before or after administration of the RPESC, as well as their administration concurrently with (i.e., at the same time as) the RPESC. In alternative embodiments, one or more growth factors and/or other endogenous factors can be administered to a patient, so as to stimulate the proliferation and differentiation of the patient's own endogenous RPESCs.

The RPESC, growth and/or exogenous factors can be administered using any delivery system described herein, as well as with other delivery systems known in the art; including delivery systems described in the above-cited application Ser. No. 12/398,888.

RPESC of the invention are also useful for cell-based models and drug screening assays for a variety of disease and disorders, including any of the diseases and disorders described in this application. Hence, the invention also provides methods that use RPESC to screen for therapeutic compounds; i.e., for compounds that are or may be useful for treating a disease or disorder of interest.

Preferred screening methods of the invention generally comprise steps of contacting an RPESC, or a cell descended from an RPESC, with a test compound, and determining whether the test compound changes or modulates (e.g., increases or decreases) one or more characteristics associated with the disease or disorder. The RPESC are preferably grown under conditions in which they exhibit one or more of the characteristics of the disease or disorder of interest. For example, the RPESC may be cultured or grown under conditions in which they differentiated into either normal or pathological cells associated with a disease or disorder of interest, or into cells exhibiting one or more normal or pathological conditions associated with the disease or disorder of interest. The one or more characteristics can include, for example, the expression level of one or more genes or gene products whose abnormal expression is associated with the disease or disorder of interest. A change or modulation of one or more of these characteristics in cells treated with the test compound, compared to cells not treated with the test compound, is indicative that the test compound may be useful for treating the disease or disorder of interest. In certain preferred embodiments a characteristic associated with the disease or disorder of interest may be the elevated expression of a particular gene or gene product, and a decreased expression of that gene or gene product in cells treated with the test compound, relative to cells not treated with the test compound, indicates that the test compound may be useful for treating the disease or disorder of interest. Alternatively, a characteristic associated with the disease or disorder may be decreased or lower expression of a particular gene or gene product, and increased expression of the gene or gene product in cells treated with the test compound, relative to cells not treated with the test compound, can indicate that the test compound may be useful for treating the disease or disorder of interest.

A particularly preferred screening assay of the invention identifies compounds that are or may be useful for treating age-related macular degeneration (AMD). A preferred characteristic associated with AMD is an elevated or increased expression of the gene αB-crystallin and its gene product. Hence, in preferred embodiments, RPESC or cells derived therefrom are used to screen for a compound to treat AMD by screening for compounds that modulate expression of the αB-crystallin gene and/or its gene product. Such screening assays involve a step of contacting a test compound to an RPESC of the invention, or to a cell derived therefrom, and determining whether the test compound modulates (e.g., increases or decreases) expression of the αB-crystallin gene or gene product compared to cells (preferably of the same cell type cultured under the same or substantially the same conditions) that are not treated with the test compound. The RPESC are preferably cultured under conditions for culturing RPE cells that also increase expression of the αB-crystallin gene or gene product. Alternatively, the RPESC may be induced to differentiate into RPE cells, e.g., as described herein, which may then be cultured under conditions that increase expression of the αB-crystallin gene or gene product. For example, the cells may be cultured under conditions of oxidative stress, such as exposure to hydrogen peroxide ($H_2O_2$) or light (e.g., blue or UV-light). In preferred embodiment, the test compound is identified as a compound for treating AMD if it decreases expression of the αB-crystallin gene or gene product in the RPESC or progeny thereof.

RPESC of the invention can also be used in cell based assays and models for other diseases and disorders; including, for example, retinitis pigmentosa, proliferative vitreoretinopathy, epiretinal membrane formation and retinitis, as well as any of the other disease and disorders described herein. Such assays and models are therefore also considered part of the invention.

DETAILED DESCRIPTION

Figure 1:
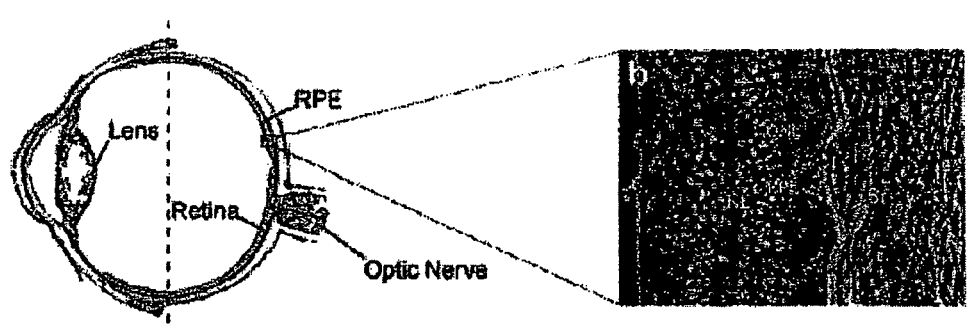
FIG. 1 is a schematic representation of a sagittal section of the adult human eye.

The present invention relates to a population of retinal pigment epithelial stem and progenitor cells isolated from the adult human retinal pigment epithelium (RPE) that can be expanded many fold in vitro and produce a wide variety of progeny from each of the major developmental lineages (endoderm, mesoderm and ectoderm). Self-renewal of these cells occurs, indicating a new kind of stem cell, the RPE stem cell (RPESC). Prior studies have shown that the eye contains progenitor cells in the ciliary margin and the iris epithelium that can produce retinal cell progeny. Reh & Fischer, *Methods Enzymol.* (2006) 419:52-73. RPESCs are distinguished from such retinal stem cells (RSCs) by their location in the main posterior retinal pigment epithelium layer, where RSCs are not found, by their lack of CHX10 staining and by their requirement for growth factors for expansion. Tropepe et al., *Science* (2000) 287:2032-2036.

Notably, while the RPESCs are capable of producing retinal cells like RSCs, they also are capable of producing a much wider repertoire of progeny, including bone, muscle and adipocytes. RPESCs appear to be a more primitive type of stem cell, which upon treatment with growth factors, express genes associated with early embryonic stem cells including Sox2. Embryonic stem (ES) cells readily produce RPE cells (Klimanskaya et al., *Cloning Stem Cells* (2004) 6:217-245) and in this sense are closely related to RPESCs. This invention establishes the human RPESC as a unique source of multipotent stem cells for the study of cell fate choice, cell replacement therapy and disease modeling.

Vision loss may be caused by disease or damage to the retina of the eye. The retina consists of a specialized layer of cells at the back of the eye where light entering the eye is sensed as an image. These cells normally respond to all aspects of the light emitted from an object and allow perception of color, shape and intensity. When normal retinal function is impaired, it may lead to a loss of color perception, blind spots, reduced peripheral vision, night blindness, photophobia, decreased visual acuity or blindness. For example, acquired immunodeficiency virus ("AIDS") patients may suffer cytomegalovirus retinitis which is caused by spread of the cytomegalovirus to the retina (Bloom et al., Medicine, 109(12): 963-968 (1988)). This and other infectious processes can lead to loss of visual field, decreased visual acuity, and blindness.

Uveitis is an inflammation of the eye which can affect the retina and can lead to decreased visual acuity. Its effects on the retina include inflamed or leaking vasculature which may appear as perivascular exudation or hemorrhage, edema of the retina, chorioretinal lesions, neovascularization or inflammatory changes in the peripheral retina. (Anglade et al., Drugs, 49(2):213-223 (1995)). Furthermore, cancers of the retina also impair vision. One example is retinoblastoma, which is a childhood type of cancer. Physical damage to retinal cells may also occur through retinal detachment which leads to retinal degeneration and blindness.

Many different genetic diseases lead to retinal damage and blindness. A relatively common example is retinitis pigmentosa ("RP"), which affects one person in four thousand worldwide. Patients with RP have normal vision for one or more decades, and then experience progressive loss of vision due to the premature death of rod or cone cells. Blindness may result. Other types of retinal degenerations (retinal dystrophies) may result from the programmed death of other retinal cell types.

Age-related macular degeneration (AMD) is a progressive degeneration of photoreceptors and their underlying RPE in the macula region of the retina, leading at end-stage to development of a disciform or an atrophic scar (Penfold et al. (2001) Prog. Retinal Eye Res. 20, 385-414; Sarks and Sarks, (1994) Chapter 67 in Retina, volume 2, Ed. S. Ryan. Publ. Mosby). At least two forms of AMD are recognized: "dry" and "wet." It is to be understood that the methods and compositions of this invention can be applied to either the dry or wet forms of AMD, or to both. Hence, the term AMD, as used herein, encompasses both these forms. In the United States, one recent estimate places the incidence of AMD at more than 11 million patients, and 1.2 million of these are legally blind with loss of central vision. Only a limited number of AMD patients are amenable to treatment despite the high incidence and severity of vision impairment (Ciulla et al. (1998) Surv. Ophthalmol. 43, 134-146). To date, there is a great need and effort to develop effective treatments or preventative measures, and to slow down or halt the progression of AMD would be a major achievement.

In certain embodiments, RPESC cultures provide useful assay cultures for toxicity testing or for drug development testing. Toxicity testing is done by culturing stem cells or cells differentiated from stem cells in a suitable medium and introducing a substance, such as a pharmaceutical or chemical, to the culture. The stem cells or differentiated cells are examined to determine if the substance has had an adverse effect on the culture. Drug development testing may be done by developing derivative cell lines, for example a pathogenic retinal cell line, which may be used to test the efficacy of new drugs. Affinity assays for new drugs may also be developed from the RPESCs, RPE progenitor cells, or differentiated cells or cell lines derived from the RPESCs or differentiated cells.

In other embodiments, RPESCs provide a culture system from which genes, proteins and other metabolites involved in cell development can be isolated and identified. The composition of stem cells may be compared with that of progenitor cells and differentiated cells in order to determine the mechanisms and compounds which stimulate production of stem cells, progenitor cells or mature cells. This invention also provides a method for stimulating stem cells of the posterior region of the retinal pigment epithelial layer to proliferate and differentiate in vivo. The cells of the present invention have the ability to recreate diverse cell types including retinal cells, neuronal cells, neural cells, bone cells, muscle cells, ectoderm, mesoderm and endoderm.

The RPESC also has utility in research not directly related to disease such as to reveal biological mechanisms, responses to environmental change or for comparison to other stem cell types. Proliferation is induced by administering one or more growth factors to the retina. Proliferation is also induced by administering genetically engineered cells which secrete growth factors into the eye. RPESCs may also be used in model systems in vitro to screen for new drugs for the treatment of diseases, such as AMD or RP.

With respect to the eye, current medical and surgical drug treatments are inadequate for restoring vision lost when retinal cells are damaged, so the potential clinical applications of pharmaceutical compositions containing RPESCs or to stimulate endogenous proliferation of RPESCs are tremendous. RPESCs would have the potential to act as in vivo targets for stimulation by growth factors in order to produce healthy tissue. This may be done, for example, by injecting growth factors or genetically engineered cells which secrete growth factors into the eye.

Figure 3:
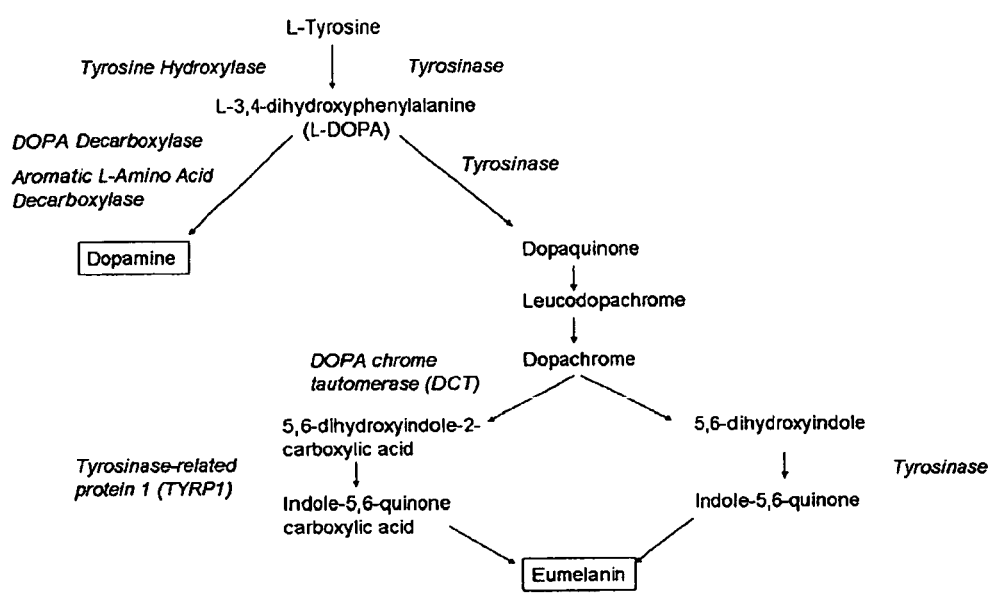
FIG. 3 illustrates the metabolic pathways of eumelanin and dopamine synthesis.

In the case of other neurological sites, such as the central and peripheral nervous system sites, there is a need in the art for the treatment of neurodegenerative disorders, and ideally treatments which do not induce unfavorable reactions, such as graft rejection or graft versus host disease in the patient. Parkinson's disease (PD), for example, is the most common neurodegenerative movement disorder [Forman et al., (2004) Nat. Med. 10:1055-1063] and is characterized by degeneration of the dopaminergic neurons in the substantia nigra pars compacta, accompanied by decreases in striatal dopamine (DA) and the appearance of intracytoplasmic Lewy body inclusions. Once striatal DA loss reaches the 80% critical value [Hornykiewicz et al., (2001) J. Chem. Neuroanat 22:3-12], a progressive motor impairment develops that is characterized by resting tremor, rigidity, bradykinesia, hypokinesia, and postural instability [Calne et al., (1992) Ann. Neurol. 32 Suppl:S125-127]. The synthesis of DA involves the enzyme tyrosine hydroxylase (TH), which converts L-Tyrosine into L-3,4-dihydroxyphenylalanine (L-DOPA), an important intermediate in the DA synthesis pathway [See FIG. 3].

In certain embodiments of the present invention, RPESCs are differentiated into midbrain dopaminergic neurons that express TH and the neural markers Nestin and Tuj1. Thus, RPESCs are useful for the treatment of PD.

Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. Spinal muscular atrophy (SMA) is a term applied to a number of different disorders, all having in common a genetic cause and the manifestation of weakness due to loss of the motor neurons of the spinal cord and brainstem. In certain embodiments, the present invention relates to the treatment of neurological or myopathic disease with an effective amount of the RPESCs of the present invention.

Leber's hereditary optic neuropathy (LHON) or Leber optic atrophy is a mitochondrially inherited (mother to all offspring) degeneration of retinal ganglion cells (RGCs) and their axons that leads to an acute or subacute loss of central vision; this affects predominantly young adult males [Nikoskelainen et al., (1995) J. Neurol. Neurosurg. Psychiatry 2:160-164]. The eye pathology is limited to the retinal ganglion cell layer especially the maculopapillary bundle. Degeneration is evident from the retinal ganglion cell bodies to the axonal pathways leading to the lateral geniculate nucleii. Experimental evidence reveals impaired glutamate transport and increased reactive oxygen species (ROS) causing apoptosis of retinal ganglion cells. Also, experiments indicate that normal non LHON affected retinal ganglion cells produce less of the potent superoxide radical than other normal central nervous system neurons [Hoegger et al., (2008) BMC Neurosci 8; 9:4].

One aspect of the present invention relates to the methods of expanding endothelial cells in vitro by co-culturing them with RPESCs. Endothelial cells are important for vascularization and angiogenesis. In yet another aspect of the invention, RPESCs transplanted onto chick chorioallantoic membrane (CAM) develop into teratomas. The CAM model of teratoma formation, as well as angiogenesis, closely mimics characteristics of these processes in humans and provides a useful tool for studying human disease.

Yet another aspect of the present invention involves progenitor cells derived from RPESCs. RPESCs are closely related to early RPE progenitors. These early progenitors are multipotential cells that may be differentiated into all of the major lineage groups including mesoderm and endoderm. Thus, bone cells and muscle cells may be generated by differentiation of RPESCs and RPE progenitor cells.

One aspect of the present invention concerns the therapeutic use of the pharmaceutical compositions of this invention to treat patients having degenerative diseases, such as age-related macular degeneration, or disorders or abnormal physical states of the eye, which includes an acceptable carrier, auxiliary or excipient. The compositions can be for topical, parenteral, local, intraocular or intraretinal use.

The pharmaceutical composition can be administered to humans or animals. Dosages to be administered depend on patient needs, on the desired effect and on the chosen route of administration.

The pharmaceutical compositions can be prepared by known methods for the preparation of pharmaceutically acceptable compositions which can be administered to patients, and such that an effective quantity of the cells is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA 1985).

On this basis, the pharmaceutical compositions could include an active compound or substance, such as growth factors, genetically engineered stem cells or retinal cells which secrete growth factor or other substances, in association with one or more pharmaceutically acceptable vehicles or diluents, and contained in buffered solutions with a suitable pH and iso-osmotic with the physiological fluids. The methods of combining growth factor or cells with the vehicles or combining them with diluents are well known to those skilled in the art. The composition could include a targeting agent for the transport of the active compound or cells to specified sites within the eye, such as specific cells, tissues or organs.

In preferred embodiments, pharmaceutical compositions of the invention can include a sustained delivery composition comprising one or more exogenous factors, for administration in combination with an RPESC of the invention or in combination with a differentiated RPESC of the invention. The exogenous factors can include, for example, at least one growth factor such as Nerve Growth Factor (NGF), Glial Cell-Line Derived Growth Factor (GDNF), Neurotrophin (NT) 3, NT4/5, NT6, Ciliary Neurotrophic Factor (CNTF), Interleukin 6 (IL6), Interleukin 11 (IL11), Cardiotrophin 1, a growth factor hormone, hyaluronidase, chondroitinase ABC (CABC), basic fibroblast growth factor (BDNF), epidermal growth factor (EGF), sonic hedgehog (Shh) or another other growth factor or other exogenous factor described throughout this specification or in U.S. patent application Ser. No. 12/398,888 filed Mar. 5, 2009 and incorporated herein by reference in its entirety.

Sustained delivery compositions comprising one or more exogenous factors can be administered concurrently with, before or after the administration of either an RPESC or a differentiated RPESC. For example, U.S. patent application Ser. No. 12/398,888 filed Mar. 5, 2009 and incorporated herein by reference describes the administration of sustained release biodegradable microspheres loaded with one or more exogenous factors such as sonic hedgehog (Shh) and/or retinoic acid in combination with neural stem cells. The use of such compositions is also contemplated in the presented invention, for administration in combination with an RPESC or a differentiated RPESC, such as an RPESC that has been differentiated into a dopaminergic or other neuron.

The present invention also relates to the use of the stem cells and progenitor cells of this invention to introduce recombinant proteins into the diseased or damaged retina. The cells act as a vector to transport a recombinant molecule, for example, or to transport a sense or antisense sequence of a nucleic acid molecule. In the case of a recombinant molecule, the molecule would contain suitable transcriptional or translational regulatory elements.

Suitable regulatory elements may be derived from a variety of sources, and they may be readily selected by one of ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule.

The recombinant molecule may be introduced into stem cells or retinal cells differentiated from stem cells of a patient using in vitro delivery vehicles such as retroviral vectors, adenoviral vectors, DNA virus vectors, amplicons and liposomes. They may also be introduced into these cells using physical techniques such as microinjection and electroporation or chemical methods such as coprecipitation and incorporation of DNA into liposomes.

Suitable regulatory elements may be derived from a variety of sources, and they may be readily selected by one of ordinary skill in the art. If one were to upregulate the expression of the gene, one would insert the sense sequence and the appropriate promoter into the vehicle. If one were to downregulate the expression of the gene, one would insert the antisense sequence and the appropriate promoter into the vehicle. These techniques are known to those skilled in the art.

The pharmaceutical compositions of the present invention could also include the active compound or substance, such as the RPESCs of this invention, or retinal progenitor cells or differentiated cells derived from those stem cells, in association with one or more pharmaceutically acceptable vehicles or diluents, and contained in buffered solutions with a suitable pH and iso-osmotic with the physiological fluids. The methods of combining cells with the vehicles or combining them with diluents is well known to those skilled in the art. The composition could include a targeting agent for the transport of the active compound to specified sites within the eye, such as specific cells, tissues or organs.

Definitions

The following definitions are provided for clarity and illustrative purposes only, and are not intended to limit the scope of the invention.

As used herein, the term "stem cell" refers to a cell that retains the ability to renew itself through mitotic cell division and can differentiate into a diverse range of specialized cell types.

As used herein, the term "plasticity" refers to the ability of an adult stem cell to adopt a variety of cell fates.

As used herein, the term "neotony" is the retention by adult cells of traits previously only seen in embryonic cells.

The term "growth factor" can be a naturally occurring, endogenous or exogenous protein, or recombinant protein, capable of stimulating cellular proliferation and/or cellular differentiation.

As used herein, the term "morphogenic factor" refers to a substance governing the pattern of tissue development and, in particular, the positions of the various specialized cell types within a tissue.

As used herein, "central nervous system" includes brain and/or the spinal cord of a mammal. The term may also include the eye, retina, and optic nerve in some instances.

As used herein, the term "neuron" as used herein describes a nerve cell capable of receiving and conducting electrical impulses from the central nervous system. A nerve cell or "neuron" may typically include a cell body, an axon, axon terminals, and dendrites.

As used herein, the term "exogenous factor" describes those compounds capable of inducing differentiation of a stem cell into another cell type. These compounds include, but are not limited to antioxidants, trophic factors, morphogenic factors, and growth factors.

As used herein, the term "agent" refers to a chemical or recombinant compound that may be used to treat a condition or disease.

As used herein, the term "autologous" refers to cells, tissues or even proteins that are isolated and reimplanted into the same individual.

As used herein, the term "non-autologous" refers to cells, tissues, or even proteins that are transplanted from one individual to another individual.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e., extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell, or cells of a different genus or species.

Expression System

The term "expression system" means a host cell and compatible vector under suitable conditions, e.g., for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., Cell 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. coli*.

Treating or Treatment

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

Patient or Subject

"Patient" or "subject" refers to mammals and includes human and veterinary subjects.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Dosage

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level.

Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO$_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/ 0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see Molecular Biology of the Cell, Alberts et al., 3rd ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO$_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, J. Mol. Biol. 1975; 98: 503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"); or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/on the WorldWideWeb. Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna. CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Variant

The term "variant" may also be used to indicate a modified or altered gene, DNA sequence, enzyme, cell, etc., i.e., any kind of mutant.

Pharmaceutically Acceptable

When formulated in a pharmaceutical composition, a therapeutic compound of the present invention can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Kits

In one embodiment, the invention relates to a kit comprising RPESCs useful for modeling a disease or condition in vitro. This kit further comprises a means for detecting improvement in the disease or condition following treatment with an agent.

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "µl" means microliter(s); "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

EXAMPLES

The following examples are included to demonstrate certain embodiments of the invention. It should be appreciated by those of skill in the art that the techniques disclosed in the examples constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

The following describes the materials and methods employed in the examples.

Isolation and Culture of Human RPE Cells.

Human ocular tissues from 60-100 year old donors were obtained from The Eye-Bank for Sight Restoration, Inc, New York, N.Y., and the National Disease Research Interchange, Philadelphia, Pa. RPE dissection and single cell dissociation was performed essentially as described. Burke et al., *Exp. Eye Res.* (1996) 62:63-73; Maminishkis et al., *Invest. Ophthalmol. Vis. Sci.* (2006) 47:3612-3624. RPE cells were transferred in non-coated 60 mm plate and cultured in Minimum Essential Medium Eagle, 2 mM L-glutamine, 1% Penicillin/Streptomycin, 1% Na-Pyruvate, 50% fetal bovine serum (FBS), 10 ng/ml FGF2 and 1 ng/ml EGF (Gibco/Invitrogen). Cells began to form spheres within 3-4 days in culture and continued to grow in mass and number. Half of the medium was changed every 4 days. For passaging of cells, the culture medium containing the floating spheres was collected in a 15-ml centrifuge tube and centrifuged at 800 to 12,400 rpm for 5 min. The pellet was resuspended in 200 to 500 µl of Accutase (Innovative Cell Technologies), triturated 5 times, placed at 37° C. for 10 min, triturated again and resuspended in medium. In some experiments, cells were grown in adherent cell culture conditions in 6-well plates coated with fibronectin (5 µg/ml)/laminin (1 µg/ml) (Gibco/Invitrogen). ARPE-19 cells, available from the American Type Culture Collection (ATCC), Manassas, Va. (Accession No. CRL-2302) were cultured in the same culture medium as described above and passed when they were confluent. The cells were incubated in a 37° C. humidified incubator under 95% air and 5% $CO_2$ and the medium was replaced every 2-3 days.

In Vitro-Induced Differentiation

RPE cells were cultured in medium designed for ES cell maintenance. They were seeded on uncoated 60 mm plates and cultured as RPESC spheres in KSR medium (Gibco) supplemented with FGF2 (20 ng/ml, Sigma-Aldrich) and incubated at 37° C. in humidified 5% $CO_2$ in air for 7 days. The medium was changed every 3 days.

For experiments in which dopaminergic neurons were generated, the following methods were used: The RPESCs were grown on gelatin-coated tissue culture plates in ES cell medium consisting of knockout DMEM supplemented with 15% FBS, 0.1 mM MEM nonessential amino acids, 0.1 mM 2-mercaptoethanol (2-ME), 2 mM L-glutamine, 1% Penicillin/Streptomycin (Gibco-Invitrogen). RPESC cells were dissociated (0.25% trypsin-EDTA) to single cells and transferred to an uncoated plate at a density of $2$-$2.5 \times 10^4$ cells $cm^2$ in knockout DMEM supplemented with 10% knockout serum replacement, 0.1 mM MEM nonessential amino acids, 0.1 mM 2-mercaptoethanol (2-ME), 2 mM L-glutamine, 1% Penicillin/Streptomycin (Gibco-Invitrogen) (KSR medium) supplemented with FGF2 (20 ng/ml, Sigma-Aldrich). KSR medium was replaced every 3 days. RPESCs were cultured under the same conditions as used for the maintenance of mouse embryonic stem cells. They were seeded on uncoated 60 mm plates and cultured in KSR medium supplemented with FGF2 (20 ng/ml, Sigma-Aldrich) and incubated at 37° C. in humidified 5% $CO_2$ in air for 7 days. The medium was changed every 3 days.

The following conditions were used to differentiate the cultured RPE into different lineage pathways, using combinations of published protocols modified as described:

Neurogenic Lineage:

RPESC spheres were seeded on uncoated plates and cultured in neural differentiation medium (N2/B27): ES-Cult™ Basal Medium-A, B-27, N2, ITS (insulin, transferrin, selenium) Supplement-B (Stemcell Technologies Inc), 1% Penicillin/Streptomycin (Gibco-Invitrogen) and supplemented with all trans retinoic acid (RA, 2 µM, Sigma-Aldrich), FGF2 (20 ng/ml, Sigma-Aldrich), FGF8b (100 ng/ml, R&D Systems), Shh (100 ng/ml, R&D Systems) for 4 days. RPE spheres were transferred into 24 well plates coated with fibronectin (5 µg/ml)/laminin (1 µg/ml) and incubated in neural differentiation medium supplemented with all growth factors except FGF2 (RA, FGF8, and Shh). The cells were maintained in neural differentiation medium for >4 weeks, with medium and growth factors changed every third day.

Osteogenic Lineage:

RPE spheres were seeded on uncoated plates and cultured in osteogenic differentiation medium: IMDM medium with 20% FBS, 0.1 mM MEM nonessential amino acids, 0.1 mM 2-ME, 2 mM L-glutamine, 1% Penicillin/Streptomycin (Gibco-Invitrogen), B-27, N2 supplement (Stemcell Technologies Inc.), and osteogenic supplements 1 nM dexamethasone, 10 mM beta-glycerophosphate and 50 µM ascorbic acid-2-phosphate (Sigma-Aldrich) for 4 days. Duplomb et al., *Stem Cells* (2007) 25:544-552; Karner et al., *Stem Cells Dev.* (2007) 16:39-52. RPE spheres were transferred onto 24 well plate coated and incubated in osteogenic differentiation medium supplemented with all osteogenic supplements. The cells were maintained in osteogenic differentiation medium for >4 weeks, with medium and osteogenic supplements changed every third day.

Myogenic Lineage:

RPE spheres were seeded on uncoated plates and cultured in myogenic differentiation medium: ES-Cult™ Basal Medium-A with 20% KO serum replacement, 0.1 mM MEM nonessential amino acids, 0.1 mM 2-ME, 2 mM L-glutamine, 1% Penicillin/Streptomycin (Gibco-Invitrogen), B-27, N2 supplement (Stemcell Technologies Inc.) and supplemented with FGF2 (20 ng/ml, Sigma-Aldrich), BMP4 (50 ng/ml, R&D Systems), BMP2 (50 ng/ml, R&D Systems) for 4 days. Hosseinkhani et al., Stem Cells (2007) 25:571-580; Yao et al., Proc. Natl. Acad. Sci. U.S.A. (2006) 103:6907-6912. The cells were maintained in myogenic differentiation medium for >4 weeks, with medium and osteogenic supplements changed every second day.

Adipogenic Lineage:

Human RPE spheres were seeded on uncoated plates and grown to confluence, followed by exposure of 0.5 mM isobutylxanthine, 1 mM dexamethasone and 10 µg/ml insulin (all from Sigma-Aldrich) in Mesencult® MSC Human Basal Medium (Stemcell Technologies Inc) containing 10% FBS for >3 weeks.

Endoderm Lineage:

Human RPE spheres were seeded on uncoated plates and cultured in endoderm differentiation medium: IMDM medium with 2 mM L-glutamine, 1% Penicillin/Streptomycin (Gibco-Invitrogen), B-27, N2, ITS Supplement-B (Stemcell Technologies Inc.), and supplemented with FGF2 (20 ng/ml, Sigma-Aldrich), BMP4 (50 ng/ml, R&D Systems), Activin (50 ng/ml, R&D Systems), 50 µM ascorbic acid (Stemcell Technologies Inc.) for 4 days. Gouon-Evans et al., Nat. Biotechnol. (2006) 24:1402-1411; Kubo et al., Development (2004) 131:1651-1662. The cells were maintained in endoderm differentiation medium for >4 weeks, with medium and supplements changed every third day.

Chondrocyte Lineage:

Chondrogenic differentiation of human RPESCs was induced with high glucose Gibco® DMEM medium (available from Invitrogen Corporation, Carlsbad, Calif.) supplemented with ITS (6.25 µg/ml insulin, 6.25 µg/ml transferring, 6.25 ng/ml selenium) (available from Stem Cell Technologies, Vancouver, British Columbia), 1.25 mg/ml bovine serum albumin, 5.35 µg/ml linoleic acid (available from BD Biosciences, San Jose, Calif.), 40 µg/ml L-proline (available from Sigma-Aldrich Corporation, St. Louis, Mo.), 50 µg/ml ascorbic acid 2-phosphate (available from Sigma, a subsidiary of Sigma-Aldrich), 1% sodium piruvate (Sigma), 1% nonessential amino acids (Gibco-Invitrogen), 10-7M dexamethason (Sigma-Aldrich) and 1% penicillin/streptomycin (Gibco-Invitrogen). After incubation for 24 hours to allow cell attachment (day 1 of differentiation), 100 ng/ml recombinant human BMP2 (available from R&D Systems, Inc., Minneapolis, Minn.) was added into the medium for a period of 21 days with media change every alternate day.

Neural Crest Lineage:

Neural crest differentiation of human RPESC was induced with DMEM/F12 medium with N2 basal medium supplemented with 2 mM L-glutamine, 1% penicillin/streptomycin (Gibco-Invitrogen), 10 ng/ml recombinant human FGF2 (Invitrogen) and 20 ng/ml recombinant human BMP2 (R&D Systems) for a period of 8 days with media change every alternate day.

Dopaminergic Neurons:

RPESCs were plated in non-adherent dishes in serum-free KSR medium supplemented with FGF2. After 2 days the medium was replaced and SHH/FGF8 was added for an additional 5 to 7 days (See FIG. 4 for a time line of neural induction).

Immunostaining

Cultured RPE cell monolayers, RPESC spheres, or differentiated RPESCs were fixed for 10 min at room temperature in 4% (w/v) paraformaldehyde in PBS. RPESC spheres were embedded in OTC (Sakura Finetek) and sectioned (12-16 µm) on a cryostat (Leica CM-3050). Cell cultures were permeabilized and blocked in PBS with 0.1% (v/v) Triton and 10% (v/v) normal goat serum for 1 hr at room temperature prior to staining with a primary antibody for 1 hr at room temperature or overnight at 4° C. (See Table 1 for description of each primary antibody and its usage). Cells were washed three times (for 15 min/wash) with PBS with 0.05% (v/v) Triton, followed by incubation with the secondary antibody for 45 min at room temperature. Nuclei were counter-stained with Hoechst 33342 (Molecular Probes). For immunohistochemical analysis of RPE adult human eyes, frozen sections were fixed and processed as described. De et al., Arch. Ophthalmol. (2007) 125:641-645. Secondary antibody staining was done using the corresponding goat anti-rabbit IgG Alexa Fluor 488, goat anti-mouse IgG Alexa Fluor 546, goat anti-mouse IgM Alexa Fluor 546 (Molecular Probes) and Rhodamine (Jackson ImmunoResearch). Phase and fluorescent images were taken with a Zeiss Axiovert 200 inverted microscope and a Zeiss AxioCam MRm digital camera with AxioVision 4 software.

TABLE 1

Antibodies for Immunocytochemistry Analysis

| Cell Type | Antibody | Dilution | Isotype | Company |
|---|---|---|---|---|
| Stem cell Marker | SSEA-4 | 1:20 | Mouse IgG3 | Chemicon[1] |
| Stem cell Marker | Nanog | 1:20 | Goat IgG | R&D System[2] |
| Stem cell Marker | Oct-4 | 1:100 | Rabbit IgG | Santa Cruz Lab[3] |
| RPE Marker | Cralbp (UW55) | 1:1000 | Rabbit IgG1 | See Stecher et al.[4] |
| RPE Marker | RPE65 | 1:200 | Rabbit IgG1 | See Hamel et al.[5] |
| RPE Marker | Mitf | 1:50 | Mouse IgG1 | NeoMarkers[6] |
| RPE Marker | PDEF | 1:50 | Mouse IgG2a | Chemicon |
| RPE, Epithelial Marker | ZO-1 | 1:100 | Rabbit IgG1 | Zymed[7] |
| RPE, Epithelial Marker | Cytokeratin | 1:800 | Mouse IgG1 | Sigma[8] |
| RPE Marker | Bestrophin | 1:100 | Mouse IgG1 | Novus Biologicals[9] |
| RPE, Retina Progenitor, Amacrine cells | Pax6 | 1:25 | Mouse IgG1 | Hybridoma Bank[10] |
| RPE, Retina Progenitor Marker | Sox2 | 1:1000 | Rabbit IgG1 | Chemicon |
| Pre-Neural Marker | Nestin | 1:200 | Mouse IgG1 | Chemicon |
| Neural Progenitor | Olig2 | 1:50 | Rabbit IgG1 | See Ligon et al.[21] |
| Neural Progenitor | Otx2 | 1:1000 | Rabbit IgG1 | Chemicon |
| Neural Marker | β-Tubullin III (Tuj1) | 1:1000 | Mouse IgG2b | Covance[11] |
| Neural Marker | Neurofilament 150DK | 1:200 | Rabbit IgG1 | Chemicon |

TABLE 1-continued

Antibodies for Immunocytochemistry Analysis

| Cell Type | Antibody | Dilution | Isotype | Company |
|---|---|---|---|---|
| Rod Photoreceptor Marker | Rhodopsin Rho 1D4 | 1:100 | Mouse IgG1 | Chemicon |
| Rod Photoreceptor Marker | Rom1C | 1:300 | Rabbit IgG1 | See Mata et al.[12] |
| Rod Photoreceptor Marker | Math5 | 1:500 | Rabbit IgG1 | Chemicon |
| Rod Photoreceptor, Bipolar cells Marker | Recoverin | 1:500 | Rabbit IgG1 | Chemicon |
| Amacrine cell Marker | NeuroD | 1:1000 | Rabbit IgG1 | Chemicon |
| Amacrine cell Marker | Syntaxin | 1:200 | Mouse IgG1 | MBL[13] |
| Amacrine cell, Horizontal cell Marker | Calbindin 28KD | 1:2500 | Rabbit IgG1 | Swant[15] |
| Horizontal cell Marker | Lim1 | 1:200 | Rabbit IgG1 | Novus Biologicals |
| Horizontal cell Marker | NF150 KD | 1:200 | Rabbit IgG1 | Chemicon |
| Horizontal cell, Bipolar cell, Amacrine cell Marker | Prox1 | 1:5000 | Rabbit IgG1 | Covance |
| Bipolar cell Marker | PKC α | 1:50 | Rabbit IgG1 | Cell Signaling[15] |
| Ganglion cell Marker | Math5 | 1:1000 | Rabbit IgG1 | Chemicon |
| Glia cell Marker | GFAP | 1:1000 | Rabbit IgG1 | Dako[16] |
| Hepatic cell Marker | α 1 fetoprotein (AFP) | 1:500 | Rabbit IgG1 | Dako |
| Smooth muscle cell Marker | α smooth muscle actin | 1:500 | Mouse IgG2 | Dako |
| Skeletal muscle cell Marker | α-actinin (sarcomeric) | 1:800 | Mouse IgG1 | Sigma |
| Striated muscle celll Marker | Light Meromyosin (MF20) | 1:20 | Mouse IgG2b | Hybridoma Bank |
| Bone cell Marker | BMP-4 | 1:100 | Mouse IgG2b | Chemicon |
| Nuclear Marker | Human Nuclei (HuNu) | 1:300 | Mouse IgG1 | Chemicon |
| Nuclear Marker | DAPI | 1:1000 | N/A | Molecular Probes[17] |
| Dopaminergic Neuron Marker | anti-Tyrosine hydroxylase | 1:100 | | Pel-Freez Biologicals[18] |
| | β-Tubulin I | 1:1000 | | Covance |
| Cardiac cell marker | Cardiac Troponin | 1:20 | Mouse IgG2a | Hybridoma Bank |
| Bone cell marker | Osteopontin | 1:50 | Mouse IgG2b | Hybridoma Bank |
| Cartilage marker | Collagen II | 1:40 | Mouse IgG1 | Chemicon |
| Neural crest marker | Sox10 | 1:200 | Rabit IgG | Affinity BioReagents[19] |
| Neural crest marker | Sox9 | 1:50 | Rabbit IgG | Chemicon |
| Mesenchymal marker, endothelial marker | Vimentin | 1:100 | Mouse IgG2a | Dako |
| Adipocyte marker | FABP4 | 1:100 | Rabbit IgG | Cayman Chemicals[20] |

Abbreviations:
[1]Chemicon ® a subsidiary of Millipore, Billerica, Maryland;
[2]R&D Systems, Inc., Minneapolis, Minnesota;
[3]Santa Cruz Biotechnology, Inc., Santa Cruz, California;
[4]Stecher et al., *J. Biol. Chem.* (1999) 247:8577-8585;
[5]Hamel et al., *J. Biol. Chem.* (1993) 268:15751-15757;
[6]NeoMarkers, Inc., Freemont, California;
[7]Zymed Laboratories, Inc., South San Francisco, California;
[8]Sigma is a subsidiary of Sigma-Aldrich Corporation, St. Louis, Missouri;
[9]Novus Biologicals LLC, Littleton, Colorodo;
[10]Developmental Studies Hybridioma Bank, University of Iowa, Iowa City, Iowa;
[11]Covance, Inc., Princeton, New Jersey;
[12]Mata et al., *Neuron* (2002) 36:69-80;
[13]MBL International Corporation, Woodburn, Massachussets;
[14]Swant, Bellinzona, Switzerland;
[15]Cell Signaling Technology, Danversa, massachussets;
[16]Dako Denmark A/S, Glostrup, Denmark;
[17]Molecular Probes, Inc., Eugene, Oregon;
[18]Pel-Freez ® Biologicals, Rogers, Arkansas;
[19]Affinity Bioreagents, Inc. is a subsidiary of Thermo-Fisher Scientific, Rockford, Illinois;
[20]Cayman Chemical Company, Ann Arbor, Michigan;
[21]Ligon et al., *J. Neuropathol. Exp. Neurol.* (2004) 63:499-509.

In Vivo Transplantation

Human RPE cells were injected (1×10⁶ cells/CAM in 50 μl of PBS plus $Ca^{2+}$ and $Mg^{2+}$) onto the CAMs of 9-10 day old White Leghorn chick embryos. Eggs were incubated for 7 days post-transplantation. CAMs with human RPE cells were fixed in 4% paraformaldehyde and cryosectioned for immunohistochemical analysis.

Reverse Transcriptase Polymerase Chain Reaction (RT-PCR)

Total RNA was extracted using an RNeasy mini kit (QIAGEN) from acutely isolated RPE and retina tissue derived from adult human donors; cultured RPE spheres, cultured RPE monolayers, and differentiated RPESC cells. cDNAs were synthesized from 50 ng of total RNA by SuperScript II Reverse Transcriptase (RT) (Invitrogen) primed with oligo (dT)12-18 according to the manufacturer's instructions. The amount of cDNA was normalized to actin mRNA. The primer sequences, annealing temperatures, and the number of cycles are shown in Table 2.

For more sensitive, quantitative, real-time RT-PCR, RNA was reverse-transcribed using a SuperScript™ First-Strand Synthesis System (Invitrogen) to synthesize cDNA, following the manufacturer's instructions. Real-time RT-PCR was carried out on an Applied Biosystems 7900 instrument in 20 µl reaction volumes containing 10 µl of SYBR® Green PCR mix (available from Applied Biosystems, Foster City, Calif.), 0.375 µM of each primer, and diluted cDNA. All primer pairs used were confirmed to approximately double the amount of product within one PCR cycle and to yield a single product of the predicted size. Primer sequences used are provided in Table 3, below. Relative mRNA levels were calculated using the comparative CT method described in the Applied Biosystems instruction manual, and presented either as percentage of housekeeping gene expression or as a percentage of biological controls. In all cases, results were essentially independent of the gene used for normalization (Gapdh).

TABLE 2

Primer Sequences Used for Reverse Transcription-Polymerase Chain Reaction Analysis

| Gene Target (GenBank No) | Primer Sequences (5'→3') | SEQ ID NO. | Product Size (bp) | Annealing Temp (° C.) | Cycles |
| --- | --- | --- | --- | --- | --- |
| h NANOG (NM_024865) | CAGAAGGCCTCAGCACCTAC GTCACTGGCAGGAGAATTTGG | 1 2 | 298 | 62° C. | 40x |
| h Oct4 (NM_002701) | CTTGCTGCAGAAGTGGGTGGAGGAA CTGCAGTGTGGGTTTCGGGCA | 3 4 | 187 | 65° C. | 35x |
| h c-MYC (NM_002467) | ACTCTGAGGAGGAACAAGAA TGGAGACGTGGCACCTCTT | 5 6 | 158 | 60° C. | 35x |
| h KLF4 (NM_004235) | TCTCAAGGCACACCTGCGAA TAGTGCCTGGTCAGTTCATC | 7 8 | 104 | 60° C. | 35x |
| h NESTIN (NM_006617) | AGGATGTGGAGGTAGTGAGA TGGAGATCTCAGTGGCTCTT | 9 10 | 266 | 60° C. | 40x |
| h MUSASHI (NM_002442) | GGCAGACTACGCAGGAAGG TTCACGTCCTCCACCGTG | 11 12 | 291 | 58° C. | 40x |
| h TUJ1 (NM_006086) | CATGGACAGTGTCCGCTCAG CAGGCAGTCGCAGTTTTCA | 13 14 | 175 | 60° C. | 35x |
| h SOX2 (NM 003106) | GGCAGCTACAGCATGATGCAG GCTCTGGTAGTGCTGGGACATG | 15 16 | 396 | 66° C. | 35x |
| h Pax6 (NM_001604) | TCCATCAGTTCCAACGGAGAAG GTGGAATTGGTTGGTAGACACTG | 17 18 | 337 | 62° C. | 35x |
| h Otx2 (NM_021728) | CCATGACCTATACTCAGGCTTCAGG GAAGCTCCATATCCCTGGGTGGAAAG | 19 20 | 211 | 62° C. | 35x |
| h NEUROD1 (NM_002500) | CGCTGGAGCCCTTCTTTG GCGGACGGTTCGTGTTTG | 21 22 | 118 | 58° C. | 35x |
| h CRX (NM_000554) | ATGATGGCGTATATGAACCC TCTTGAACCAAACCTGAACC | 23 24 | 263 | 60° C. | 35x |
| h ATHO7 (Math5) (NM_145178) | TCGCATCATCAGACCTATGG CCGAACAGGACAAACTCACA | 25 26 | 245 | 60° C. | 40x |
| h PEDF (NM_002615) | GGA CGC TGG ATT AGA AGG CAG TTG TAT GCA TTG AAA CCT TAC AGG | 27 28 | 1472 | 65° C. | 35x |
| h RECOVERIN (NM_002903) | CCAGAGCATCTACGCCAAGT CACGTCGTAGAGGGAGAAGG | 29 30 | 186 | 60° C. | 40x |
| h RHODOPSIN (NM_000539) | TCATCATGGTCATCGCTTTC CATGAAGATGGGACCGAAGT | 31 32 | 100 | 60° C. | 40x |
| h S-OPSIN (NM_001708) | GATGAATCCGACACATGCAG CTGTTGCAAACAGGCCAATA | 33 34 | 103 | 55° C. | 40x |
| h CHX10 (NM_182894.1) | AGCTAGAGGAGCTGGAGAAG CATGATGCCATCCTTGGCTG | 35 36 | 259 | 57° C. | 35x |
| h MASH1 (NM_004316) | CGGCCAACAAGAAGATGAGT GCCATGGAGTTCAAGTCGTT | 37 38 | 168 | 60° C. | 35x |

TABLE 2-continued

Primer Sequences Used for Reverse Transcription-Polymerase Chain Reaction Analysis

| Gene Target (GenBank No) | Primer Sequences (5'→3') | SEQ ID NO. | Product Size (bp) | Annealing Temp (° C.) | Cycles |
| --- | --- | --- | --- | --- | --- |
| h RPE65 (NM_000329) | CCTTTCTTCATGGAGTCTTTG<br>ATTGCAGTGGCAGTTGTATTG | 39<br>40 | 390 | 52° C. | 35x |
| h VEGF (NM_001025366) | TTGCCTTGCTGCTCTACCTC<br>AAATGCTTTCTCCGCTCTGA | 41<br>42 | 547 | 65° C. | 35x |
| h CRALBP (NM_000326) | ATGTCAGAAGGGGTGGG<br>TCAGAAGGCTGTGTTCTCA | 43<br>44 | 953 | 60° C. | 40x |
| h BESTROPHIN (NM_004183) | GGCCAGATCTATGTACTGGAATAAGCCCGAGC<br>GGCCCTCGAGTTAGGAATGTGCTTCATCCCTG | 45<br>46 | 773 | 65° C. | 40x |
| h SIX3 (NM_005413) | GGAATGTGATGTATGATAGCC<br>TGATTTCGGTTTGTTCTGG | 47<br>48 | 139 | 52° C. | 35x |
| h AFP (NM_001134) | TTGCTGCAAAGCTGAAAATG<br>GCAGCATTCTGTTATTTTGTTTGAC | 49<br>50 | 337 | 54° C. | 35x |
| h BRACHYURY (NM_003181) | TGCTTCCCTGAGACCCAGTT<br>GATCACTTCTTTCCTTTGCATCAAG | 51<br>52 | 120 | 54° C. | 35x |
| h MESP1 (NM_018670) | CTCGTCTCGTCCCCAGACTCAT<br>AGTTTCTCCCGCTCACTGGC | 53<br>54 | 172 | 60° C. | 35x |
| h BMP-4 (NM_130851) | CATGCTAGTTTGATACCTGAGACG<br>CTGAGGTTAAAGAGGAAACGAAAAG | 55<br>56 | 376 | 54° C. | 35x |
| h RUNX2 (NM_004348) | TCTGGCCTTCCACTCTCAGT<br>GACTGGCGGGGTGTAAGTAA | 57<br>58 | 161 | 54° C. | 35x |
| h BSP (NM_004967) | CGGAGGAGACAATGGAGAAG<br>GACGCCCGTGTATTCGTACT | 59<br>60 | 226 | 54° C. | 35x |
| h OPN (BC022844) | TGAATCTGATGAACTGGTCACTGA<br>GGTGATGTCCTCGTCTGTAGC | 61<br>62 | 190 | 54° C. | 35x |
| h COL I (NM000088) | AGACACTGGTGCTAAGGGAGAG<br>GACCAGCAACACCATCTGCG | 63<br>64 | 182 | 54° C. | 35x |
| h aSMA (NM_001102) | GTGCAGGAGAAGTGCCAGCT<br>GAGGGTGGCGGTCTCATAGT | 65<br>66 | 300 | 62° C. | 35x |
| h PPARg (NM_015869) | CTCCTATTGACCCAGAAAGC<br>GTAGAGCTGAGTCTTCTCAG | 67<br>68 | 350 | 57° C. | 35x |
| h GAPDH (NM_002046) | CCCCTTCATTGACCTCAACTACA<br>TTGCTGATGATCTTGAGGCTGT | 69<br>70 | 342 | 60° C. | 35x |
| h TFAP2A (NM_001032280) | TCCCTGTCCAAGTCCAACAGCAAT<br>AAATTCGGTTTCGCACACGTACCC | 71<br>72 | 396 | 52° C. | 35x |
| h ERBB3 (NM_001982) | GGTGCTGGGCTTGCTTTT<br>CGTGGCTGGAGTTGGTGTTA | 73<br>74 | 365 | 57° C. | 35x |
| h PAX3 (NM_181459) | GCACTGTACACCAAAGCACG<br>TAGGTGGGTGGACAGTAGGA | 75<br>76 | 349 | 57° C. | 35x |
| h SNAI2 (NM_003068) | AGCGAACTGGACACACATAC<br>TCTAGACTGGGCATCGCAG | 77<br>78 | 410 | 57° C. | 35x |
| h SNAI1 (NM_005985) | CTCCTCTACTTCAGCCTCTT<br>CTTCATCAAAGTCCTGTGGG | 79<br>80 | 611 | 52° C. | 35x |
| h SOX10 (NM_006941) | ATACGACACTGTCCCGGCCCTAAA<br>TTCTCCTCTGTCCAGCCTGTTCTC | 81<br>82 | 250 | 62° C. | 35x |
| h PAX7 (NM_013945) | CAGGAGACCGGGTCCATC<br>CGAACTTGATTCTGAGCACG | 83<br>84 | 216 | 58° C. | 35x |
| h Actin | TGCGTGACATTAAGGAGAAG<br>TGAAGGTAGTTTCGTGGATG | 85<br>86 | 258 | 52° C. | 35x |

TABLE 2-continued

Primer Sequences Used for Reverse Transcription-Polymerase Chain Reaction Analysis

| Gene Target (GenBank No) | Primer Sequences (5'→3') | SEQ ID NO. | Product Size (bp) | Annealing Temp (° C.) | Cycles |
| --- | --- | --- | --- | --- | --- |
| h EN1 | CCGCACCACCAACTTTTTCAT<br>TGGACAGGGTCTCTACCTGC | 87<br>88 | 171 | 60° C. | 35x |
| m EN1 | TCAAGACTGACTCACAGCAACCCC<br>CTTTGTCCTGAACCGTGGTGGTAG | 89<br>90 | 376 | 60° C. | 35x |
| h EN2 | ATCCCCTAAGCTCCAT<br>AGGAGGGAGTTAGGTG | 91<br>92 | 431 | 57° C. | 35x |
| m EN2 | CTTCTTCAGGTCCCAGGTCC<br>CTCTGTCAGGTACCTGTTGG | 93<br>94 | 136 | 58° C. | 35x |
| h TH | GAGTACACCGCCGAGGAGATTG<br>GCGGATATACTGGGTGCACTGG | 95<br>96 | 278 | 62° C. | 35x |
| m TH | TCCTGCACTCCCTGTCAGAG<br>CCAAGAGCAGCCCATCAAAGG | 97<br>98 | 423 | 60° C. | 35x |
| h Nurr1 | TTCTCCTTTAAGCAATCGCCC<br>AAGCCTTTGCAGCCCTCACAG | 99<br>100 | 332 | 60° C. | 35x |
| m Nurr1 | CTGGCTATGGTCACAGAGAG<br>ACAGGTAGTTGGGTCGGTTC | 101<br>102 | 132 | 58° C. | 35x |
| h Pax2 | ATGTTCGCCTGGGAGATTCG<br>GCAAGTGCTTCCGCAAACTG | 103<br>104 | 429 | 58° C. | 35x |
| m Pax2 | CCAAAGTGGTGGACAAGATTGCC<br>GGGATAGGAAGGACGCTCAAAGAC | 105<br>106 | 544 | 60° C. | 35x |
| h Sox1 | CAATGCGGGGAGGAGAAGTC<br>CTCTGGACCAAACTGTGGCG | 107<br>108 | 464 | 60° C. | 35x |
| m Sox1 | CCTCGGATCTCTGGTCAAGT<br>TACAGAGCCGGCAGTCATAC | 109<br>110 | 593 | 58° C. | 35x |
| h Ptx3 | ACTAGGCCCTACACAC<br>TTTTTTTGACAGTCCGC | 111<br>112 | 160 | 55° C. | 35x |
| m Ptx3 | AGGACGGCTCTCTGAAGAA<br>TTGACCGAGTTGAAGGCGAA | 113<br>114 | 372 | 60° C. | 35x |
| m Tuj1 | TCAGCGATGAGCACGGCATA<br>CACTCTTTCCGCACGACATC | 115<br>116 | 300 | 58° C. | 35x |
| m Nextin | GGAGAGTCGCTTAGAGGTGC<br>TCAGGAAAGCCAAGAGAAGC | 117<br>118 | 326 | 58° C. | 35x |

Abbreviations: Tuj1, β-tubulin III; CRALBP, cellular retinaldehyde binding protein; PEDF, pigment epithelium derived factor; VEGF, vascular endothelial growth factor; PPARγ, peroxisome proliferative activated receptor gamma; GAPDH, glyceraldehyd-3-phosphate dehydrogenase; αSMA, alpha smooth muscle actinin; BSP, bone sialoprotein; AFP, α-fetoprotein; bp, base pair; h, human; m, murine.

TABLE 3

Primer Sequences Used for Quantitative Real-Time RT-PCR Analysis

| Gene Target (GenBank No) | Primer Sequences (5'→3') | SEQ ID NO. | Product Size (bp) | Annealing Temp | Cycles |
| --- | --- | --- | --- | --- | --- |
| Human qOct4 (NM_002701) | AGCGAACCAGTATCGAGAAC<br>TTACAGAACCACACTCGGAC | 119<br>120 | 187 | 60.6° C. | 40x |
| Human qSox2 (NM_003106) | AGCTACAGCATGATGCAGGA<br>GGTCATGGAGTTGTACTGCA | 121<br>122 | 130 | 60.0° C. | 40x |
| Human qNanog (NM_024865) | TGAACCTCAGCTACAAACAG<br>TGGTGGTAGGAAGAGTAAAG | 123<br>124 | 124 | 60.7° C. | 40x |

TABLE 3-continued

Primer Sequences Used for Quantitative Real-Time RT-PCR Analysis

| Gene Target (GenBank No) | Primer Sequences (5'→3') | SEQ ID NO. | Product Size (bp) | Annealing Temp | Cycles |
|---|---|---|---|---|---|
| Human qMYC (NM_002467) | ACTCTGAGGAGGAACAAGAA TGGAGACGTGGCACCTCTT | 125 126 | 158 | 60.3° C. | 40x |
| Human qKLF4 (NM_004235) | TCTCAAGGCACACCTGCGAA TAGTGCCTGGTCAGTTCATC | 127 128 | 104 | 60.1° C. | 40x |
| Human qLIN28 (NM_024674) | AGGCGGTGGAGTTCACCTTTAAGA AGCTTGCATTCCTTGGCATGATGG | 129 130 | 189 | 60.1° C. | 40x |
| Human qGAPDH (NM_002046) | CCCCTTCATTGACCTCAACTACA TTGCTGATGATCTTGAGGCTGT | 131 132 | 154 | 60.1° C. | 40x |

(A) Isolation and Characterization of Retinal Pigment Epithelial Stem Cells (RPESC)

Figure 2:
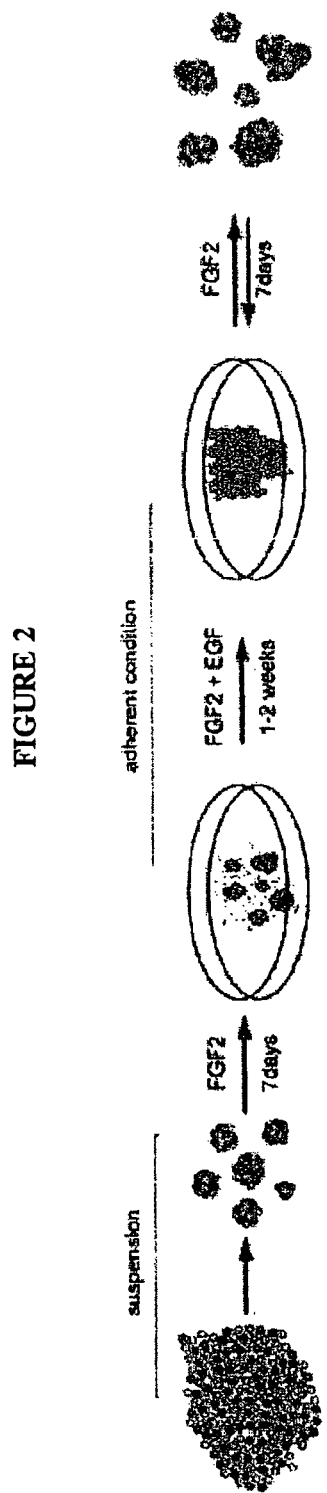
FIG. 2 demonstrates the experimental procedure used to generate RPE and RPESC cultures.

To determine whether human RPE contains stem/progenitor cells, RPE was isolated from human adult eye donors, dissociated to single cells and cultured in non-adherent conditions permissive for floating, multi-cell neurosphere formation (FIG. 2). Reynolds & Rietze, Nat. Methods (2005) 2:333-336. About 5-10% of cells proliferated to form small sphere colonies composed of darkly pigmented cells which after 7 days were larger and included nonpigmented cells.

To demonstrate that these floating spheres were RPE progenitor cells, they were plated in conditions typically used to culture adult human RPE cells. The floating sphere colonies were collected and transferred to fibronectin/laminin coated plates where they attached and proliferated further. After 1-2 weeks they formed contact-inhibited monolayers of cells with an epithelial or fusiform morphology that were lightly pigmented, typical of cultured RPE. Burke et al., Exp. Eye Res. (1996) 62:63-73. They expressed an array of characteristic RPE markers, including RPE65, Mitf, Pax6, Cralbp, Otx2 and Bestrophin. Martinez-Morales et al., Bioessays (2004) 26:766-777; Ohno-Matsui et al., Mol. Vis. (2005) 11:1-10. ARPE-19 cells, a cell line derived from RPE cells [Dunn et al., Exp. Eye Res. (1996) 62:155-169], were used as a positive control.

(B) Plasticity

The plasticity of the cultured human RPESCs was tested. Starting with either adherent or sphere-cultured RPE cells, the cells were dissociated to single cells and the resulting cell suspension was replated into KSR medium, which is formulated to grow embryonic stem (ES) cells, in non-adherent conditions. These passaged RPE cells created growing sphere colonies (henceforth called RPESC spheres) that were fixed at 7 days and sectioned for immunohistochemistry. The RPESC sphere cells expressed the neural progenitor marker Nestin which RPE cells do not normally express in vivo, implying that they had acquired a neural progenitor fate. Some of the cells expressed Pax6, which is a master regulator of eye development. Pax6 is downregulated early during RPE generation and is not normally expressed in adult human RPE; however, some Pax6+ cells in RPE cultures were observed.

(C) Markers and Phenotypes

It was also found that RPESCs showed immunoexpression of markers characteristic of ES cells (Wang et al., Nature (2006) 444:364-368; Carpenter et al., Cloning Stem Cells (2003) 5:79-88): SSEA-4 and Sox2, which is expressed by both ES cells and neural progenitor cells. Sox2 expression was predominantly cytoplasmic in some cells, though it may be noted that Sox2 can be cytoplasmic in preimplantation embryos and in developing lens fiber cells. Avilion et al., Cloning Stem Cells (2003) 5:79-88; Hever et al., Clin. Genet. (2006) 69:459-470. Western blot analysis of normal RPE tissue samples showed that the RPE tissue expresses c-Myc, but does not express Oct4, Nanog, Sox2 or KLF4. RPESCs, however, do express Sox2, KLF4 and c-Myc, but do not express significant amounts of either Oct4 or Nanog.

Quantitative PCR analysis confirmed that Oct4 is not expressed in RPESCs, in RPE primary cells, in RPE tissue, or in retina tissue. However, a very low expression of both Nanog and Lin28 was detected in retina tissue. Low expression of Sox2 was detected in RPESCs, in RPE primary cells, and in RPE tissue. Slightly higher Sox2 expression levels were detected in retina tissue. Higher expression levels of c-Myc and KLF4 were detected in RPESCs, in RPE primary cells and in RPE tissue compared to the expression of those markers in ES cells. However, no expression of those genes was detected in retina tissue. The marker CHX10 was detected in retina tissue by PCR, but was not detected in either RPESC or in normal RPE cells.

Hence, RPESC cells can express three out of five stem cell genes shown to be necessary for cell reprogramming. Takahashi et al., Cell (2007) 131:861-872; Maherali et al., Cell Stem Cell (2007) 1:55-70. The fact that RPE cells can be readily differentiated from huES cells (Klimanskaya et al., Cloning Stem Cells (2004) 6:217-245) demonstrates that there is a close relationship between these two cell types, and may reflect the very early ontogeny of RPE in vivo.

(D) Tests for Differentiation Potential

Human RPESCs were tested for their retinal differentiation potential. RPESC spheres were transferred into fresh neural differentiation medium supplemented with FGF2, FGF8, SHH and RA, conditions shown to promote retinal differentiation from ES cells (Osakada et al., Nat. Biotechnol. (2008) 26:215-224), then plated onto fibronectin/laminin coated plates in the same medium. After 3-4 days, spheres had begun to flatten and the majority of the cells expressed Nestin, Sox2 and Olig2, a neural retina progenitor marker. RT-PCR at this stage also showed expression of mRNA for neural progenitor markers Nestin, Musashi, Sox2 and Pax6, but no expression of markers of postmitotic retinal cells, including Math5, Recoverin, Rhodopsin, Crx, PKC-α, NeuroD and Prox1.

(E) Marker Expression

After a further 2-3 weeks of differentiation, the cells had acquired a variety of morphologies that, while not being typical of neurons, were clearly no longer RPE-like. The cells now abundantly expressed the neuronal marker TuJ1 and cell-type specific markers for a variety of postmitotic retinal neurons, including Recoverin, Rom1c, Rho1D4, PKCα, Pax6, Syntaxin, Prox1, Lim1, Calbindin, Neurofilament-M (NF150α) and Math5. Only rare cells (<2%) expressed GFAP, a retinal Müller glial cell marker. GFAP, Tuj1, and these other neural retinal markers are not normally expressed in RPE cells in vivo, demonstrating the plasticity of these cells after this culture regime. RT-PCR confirmed expression of markers for postmitotic retinal neurons. Notably, expression of the retinal marker CHX10 was induced after culturing the RPESC in retinal differentiation conditions as described here, even though CHX10 was not expressed in the original RPESC.

(F) Test for Multipotency

RPESC cells were further tested to determine if they are more broadly multipotent. Spheres were grown in culture conditions that are typically used to push ES cells into different lineages, corresponding to the mesoderm (myogenic, osteogenic, chondrogenic and adipogenic) endoderm (hepatic) lineages, and neural crest cells. Trounson, *Endocrine Reviews* (2006) 27:208-219. RPESC spheres were cultured in non-adherent conditions in each of the differentiation media tested, then after 4-5 days they were seeded onto gelatin coated plates in the same medium to promote differentiation for one to three weeks.

RPESCs that had been exposed to endoderm conditions, in medium supplemented with FGF2, BMP4, activin and ascorbic acid, after three weeks expressed the hepatic marker α-fetoprotein (AFP). Expression of mRNA coding for AFP marker was also detected.

(G) Myogenic Lineages

RPESCs were induced to differentiate into myogenic lineages using medium supplemented with FGF2, BMP2 and BMP4. After one week of differentiation, early myogenic markers were observed by RT-PCR, including Brachyury and Mesp1. After 3 weeks of differentiation, RPE cells adopted myofibroblast morphologies. Cells in these cultures stained positive for the smooth muscle marker α-SMA, which is not expressed in RPE cultures, and for the skeletal muscle marker sarcomeric α-actinin, and cells were occasionally positive for cardiac troponin marker cardiomyocyte marker MHC (MF20) but there was no detectable expression of NKx2.5, Myh7, Troponin 1 and Myf5.

(H) Adipocytic, Osteogenic and Chondrogenic Lineages

RPESC were also shown to be capable of adipocytic differentiation. After culturing in medium supplemented with isobutylxanthine, dexamethason and insulin the cells accumulated lipid droplets, which were detected by staining with Oil Red fluorescent dye. Cells in these cultures also stained positive with the lipid fluorescence marker HCS LipidTox™ (available from Molecular Probes, Inc., Eugene, Oreg.), and for fatty acid binding protein 4 (FABP4), an adipocyte marker. Osteogenic differentiation was induced with medium supplemented with dexamethasone, β-glicerophosphate and ascorbic acid-2-phosphate. After 3 weeks of differentiation, RPESCs expressed the osteogenic markers BMP4 and osteopontin. Mineral deposition was also detected in these cells by Alizarin red staining. Expression of mRNA coding for osteogenic markers BMP4, BSP, Rnx2, Opn and Collagenase 1 was detected. Finally, after chondrogenic differentiation RPESC showed glicosaminoglycan accumulation, detected by staining with Alcian Blue dye, and also expressed the chondrogenic marker Collagen II. The meso, endo or osteo markers were not found in RPE cells cultured in serum-containing medium.

(I) Neural Crest Lineage

RPESC were also induced to differentiate in mesenchymal cell-like and neural crest cells using medium supplemented with FGF2 and BMP2. After one week of differentiation, neural crest markers were observed by RT-PCT, including Pax7, Pax3, Sox10, ErbB3 and TFAP2A, as well as SNAI1 and SNAI2, which regulate changes in gene expression patterns underlying epithelial-mesenchymal transition (EMT). Cells were stained for the mesenchymal marker vimentin and for neural crest markers Sox9 and Sox10.

(J) Dopaminergic Neurons

In human, melanin pigment is biosynthesized in the neuroectodermic RPE and neural crest-derived melanocytes. Melanins in RPE are mainly eumelanin. Melanin-synthesizing cells contain specific organelles, the premelanosomes, in which glycoproteinic transmembrane tyrosinase catalyzes melanin biosynthesis. Enzymes involved in eumelanin biosynthesis include tyrosinase (TYR), tyrosinase-related-protein-1 (TRP1) and tyrosinase-related-protein-2 (TRP2) [Lu et al., (2007) Mol. Vis. 13:2066-2072]. Tyrosinase is the rate limiting enzyme of melanin biosynthesis and catalyses the first two steps of melanin synthesis: hydroxylation of L-tyrosine to L-3,4-dihydroxyphenylalanine (L-DOPA), and the oxidation of L-DOPA to DOPAquinone and the oxidation of 5,6-dihydroxyindole to 5,6-dihydroxyquinone (FIG. 3) [Ando et al., (2007) J. Invest. Dermatol. 127:751-761]. It is assumed that RPE melanogenesis is only found prenatally. However, tyrosinase activity has been found in adult cultured human RPE cells. TYR gene can be upregulated in response to different growth factors such as pigment epithelium-derived factor (PEDF), FGF2, a-melanocyte-stimulating hormone (a-MSH), L-tyrosine, verapamil, cholera toxin or phagocytosis of rod outer segments (ROS) by RPE cells in vitro [Julien et al., (2007) Graefes Arch. Clin. Exp. Ophthalmol 245:1495-1505]. Little is known about the expression of TYR, TPR1 and TPR2 genes involved in melanin biosynthesis in cultured RPE cells.

The concept of cell replacement to compensate for cell loss and restore functionality has entered several disease entities including neurodegenerative disorders. Parkinson's Disease (PD) is the most common neurodegenerative movement disorder [Forman et al., (2004) Nat. Med. 10:1055-1063] and is characterized by degeneration of the dopaminergic neurons in the substantia nigra pars compacta, accompanied by decreases in striatal dopamine (DA) and the appearance of intracytoplasmic Lewy body inclusions. Once striatal DA loss reaches the 80% critical value [Hornykiewicz et al., (2001) J. Chem. Neuroanat 22:3-12], a progressive motor impairment develops that is characterized by resting tremor, rigidity, bradykinesia, hypokinesia, and postural instability [Caine et al., (1992) Ann. Neurol. 32 *Suppl*: S125-127]. L-DOPA is produced as an intermediate in the eumelanin synthesis pathway, from the metabolism of tyrosine through the action of tyrosinase enzyme (FIG. 3) [Dryja et al., (1978) Invest. Ophthalmol. Vis. Sci 17:511-514; Smith et al., (1998) Exp. Eye. Res. 66:403-410]. L-DOPA can be excreted by the cell or further metabolized into dopaquinone, the next step in melanin synthesis. RPE can differentiate into different cell types depending on the combination of growth factors. The data demonstrate that RPESC can differentiate into dopaminergic neurons and represent a model for cell replacement therapy for PD.

The RPESCs of the current invention can provide a constant source of dopamine replacement via the melanin synthetic pathway enzyme tyrosinase. The transplantation of RPE cells, from which RPESCs are isolated, in rat and monkey models of PD showed an alleviation of symptoms;

however, several months later the symptoms returned because the RPE cells eventually died in the striatum. In one experiment, RPESCs are optimized for the production of levodopa and neurotrophic factors in order to survive in the striatum while providing a neuroprotective effect.

The data demonstrate that RPESCs differentiate into dopaminergic neurons when cultured in the presence of the appropriate factors. These dopaminergic neurons have the capacity to provide a continuous source of dopamine and to provide neurotrophic support that can modify PD progression. The generation of ventral midbrain and hindbrain type neurons requires the ventralizing signal sonic hedgehog (SHH) in conjunction with factors that define anterior patterning (such as FGF8 or FGF4).

Figure 4:
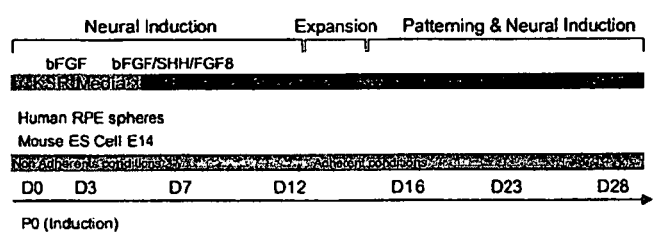
FIG. 4 is a schematic representation of neural induction progression in vitro in the presence of FGF2 (also referred to as bFGF) and SHH/FGF8.

To differentiate RPESC, a time course strategy for neural induction was developed in order to monitor the expression of specific markers (FIG. 4). RPESC and murine embryonic stem ("mES") cells were plated separately in non-adherent dishes to form spheres in KSR medium supplemented with FGF2. After 2 days the medium was replaced and SHH/FGF8 was added for an additional 5 to 7 days.

The RPESC spheres and mES cells were then used for immunocytochemistry and RT-PCR analysis. RPESC spheres and mES cells demonstrated an increase in the expression of neuronal marker class III β-Tubulin (Tuj1) and Nestin as compared to controls after 5 days incubation with SHH/FGF8. TH was expressed in the control RPESC spheres and its expression was increased after 5 days of SHH/FGF8 treatment. However, TH expression was not observed in either control or SHH/FGF8 treated mES cells.

After 12 days in culture with SHH/FGF8, more than 90% of the RPESC and mES cells expressed the neural progenitor markers Sox2, Olig2 and Tuj1, indicating that a majority of the cells were neuronal. However, less than 2% of the RPESC and mES cells were positive for TH expression, indicating a longer incubation with SHH/FGF8 was necessary.

Gene expression analysis from day 0 to day 7 of differentiation showed that midbrain markers in both RPESC and mES cells were not expressed in control conditions (N2 medium without growth factors). However, some TH expression was observed in RPESC. After 7 days in the presence of SHH/FGF8, some differences in the expression of midbrain progenitor markers was observed. Pax2 expression was not found in RPE cells, En1 expression was not found in mES cells, and dopaminergic markers (Nurr1, TH and Ptx3) were found in RPE cells but only Nurr1 was found in mES cells. These data indicate that RPESCs have the capacity to express markers of midbrain dopaminergic neuron development after 7 days in the presence of SHH/FGF8. These markers were readily detected in the hRPE cells during this period but were not expressed in the mES cell.

The data further indicate that RPESCs have the capacity to express midbrain dopaminergic markers after 7-12 days of culture in the presence of SHH/FGF8.

The ability to generate dopaminergic neurons that continuously release dopamine is an important step toward exploring the potential of human RPESCs in preclinical models of Parkinson's disease.

In another experiment, the yield of cultured midbrain dopaminergic neurons is improved. The RPESCs are co-cultured with stromal cells (MS5) derived from bone marrow. These cells have been shown to promote neural differentiation in mouse, monkey and human ES cells. Cells in these structures express markers compatible with a neural plate identity and show extensive capacity for self-renewal.

In another experiment, RPESCs are differentiated into dopaminergic neurons using a protocol adapted from Perrier et al., (2004) *Proc. Natl. Acad. Sci. USA* 101:12543-12548, in which the addition of factors such as ascorbic acid, BDNF, TGF β3, and cAMP are added to the culture to improve the yield of dopaminergic neurons.

In yet another experiment, the expression of TYR, TPR-1 and TPR2 genes, which are involved in the eumelanin biosynthesis pathway, and the expression of key transcription factors such as Pax2, Pax5, and En1, during neural induction and in committed dopaminergic precursors is determined by qPCR and immunofluorescence microscopy. Furthermore, the markers for dopaminergic neurons such as MAP2, AADC, VMAT2 are used to characterize the cells during the different stages of midbrain differentiation.

(K) In Vivo Characteristics

The in vivo potential of human RPESCs was tested after transplantation into the chick chorioallantoic membrane (CAM), a highly vascularized tissue that supports the growth of teratomas. Auerbach et al., *Int. J. Cancer* (1975) 15:241-245. The CAM is widely accepted to be an advantageous in vivo model for studying cancer, development, ophthalmology, and other research related to the retina [See Leng et al. 2004 24: (3); 427-434]. RPESC spheres were grafted into the CAM of H&H stage 22-34 chick embryos. After 7 days the RPE cells had formed a mass that was clearly vascularized. Immunostaining using human-specific antibodies show cells within the mass expressing Nestin, AFP, and αSMA, indicating multi-lineage differentiation.

RPESC were also transplanted under the skin of nude mice. Notably, these transplanted RPESC did not form tumors, and no evidence of tumor formation was observed. Other stem cells, including embryonic stem cells (ESC) and induced pluripotent stem cells (iPSC), readily form tumors in such transplantation experiments. Hence, RPESC of the invention may have a reduced capacity to form tumors in vivo, e.g., in cell transplant therapies. As such, the RPESC provide a significant advantage over ESC, iPSC and other stem cells, since they may be less likely to form tumors in cell transplant therapies.

(L) Screening Assays Using RPESC

As explained above, RPESC of the invention are useful, inter alia, as models for a variety of diseases and disorders, including as in vitro (e.g., cell culture based) models. The invention therefore encompasses the use of RPESC in such models, including cell cultures comprising RPESC and/or cells derived from RPESC. The invention also encompasses uses of such models, including cell-based screening assays that are based on these models.

Generally speaking, such assays involve culturing RPESC of the invention under conditions such that the cells exhibit one or more characteristics of a disease or disorder of interest. For example, RPESC may be cultured or grown under conditions in which they differentiate into either normal or pathological cells associated with a disease or disorder of interest, or into cells exhibiting one or more normal or pathological characteristics associated with that disease or disorder. The RPESC, or the cells derived therefrom, may then be contacted with one or more test compounds, e.g., by incubating or culturing the cells in the presence of the test compound. The cells should be contacted with the test compound under conditions and for a period of time sufficient to permit the test compound to modulate the characteristic or characteristics associated with the disease or disorder. Preferably, another preparation or culture of the RPESC (or of the cells derived therefrom) should be cultured under identical conditions but either in the absence of the test compound or, alternatively, in the presence of a suitable "placebo" compound that does not effect the characteristic or characteristics associated with the disease or disorder. The test compound's effect on the characteristic or characteristics associated with the disease or disorder is then ascertained, typically by determining the status of the characteristic or characteristics in cells treated with the test compound, and comparing them to the characteristic or characteristics in cells that either were not treated with a compound or were treated with the placebo. A change of the characteristic or characteristics in cells treated with the test compound, compared to cells that have not been treated with the test compound (e.g., in cells treated only with a placebo) indicates that the test compound may be useful, e.g., as a therapeutic agent for treating or modulating one or more effects of the disease or disorder. Preferably the change or changes observed are ones associated with amelioration of the disease or disorder, indicating that the test compound may be useful as a therapeutic agent for treating or ameliorating the disease or disorder.

For example, in many preferred embodiments the characteristic or characteristics observed in such screening assays will be one or more genes or gene products, whose abnormal expression is associated with the disease or disorder of interest. Screening assays of the invention can then be used to determine whether a test compound increases, decreases or otherwise modulates expression of one or more of these genes or gene products. Preferably, the change will be a change whose nature or direction is associated with amelioration of the disease or disorder of interest; or it may be a change whose nature or direction is opposite to the pathological change associated with the disease or disorder. Thus, for example, in embodiments where the characteristic(s) include a gene or gene product whose expression is elevated in pathological cells compared to its expression in normal cells, a test compound identified in a screening assay may decrease expression of that gene or gene product in the cells treated with that compound. Conversely, in embodiments where the characteristic(s) include a gene or gene product whose expression is decreased in pathological compared to normal cells, a test compound identified in the screening assay may increase expression of that gene or gene product in the treated cells.

As an example, and not by way of limitation, age-related macular degeneration (AMD) is associated with abnormally high accumulation of "drusen," deposits of extracellular material, on the Bruch's membrane beneath the RPE. Proteolytic analysis of drusen has indicated that certain proteins, in particular the protein αB-crystallin, are present at high levels in drusen from the eyes of patients with AMD then in drusen from eyes of normal (non-AMD affected) donors. De et al., *Arch. Opthalmol.* (2007) 125:641-646. Hence, elevated expression of the αB-crystallin gene and/or its gene product is one characteristic of AMD.

In certain preferred embodiments, therefore, RPESC, or cells derived therefrom, can be used to screen for compound to treat AMD by screening for compounds that modulate expression of the αB-crystallin gene, or its gene product, in those cells. For example, RPESC of the invention may be cultured under suitable conditions, such as the conditions described by De et al., supra, for culturing RPE cells. Alternatively, RPESC of the invention may be cultured under conditions that promote their differentiation into RPE or RPE-like cells (see, e.g., supra in these examples), which may then be cultured under conditions for culturing RPE cells. Preferably, the cultured cells are exposed to conditions that induce a pathological state or states associated with AMD and, in particular, increase expression of the αB-crystallin gene or gene product. For example, the cells may be cultured or exposed to conditions of oxidative stress, such as exposing them to hydrogen peroxide ($H_2O_2$), light (e.g., blue or UV-light) and/or other agents of oxidative stress.

These cell cultures can then be contacted with one or more test compounds to determine if any of those compounds may be useful for treating AMD. In particular, a test compound that modulates expression of αB-crystallin gene or gene product in these cells can be identified as a compound that is useful (or potentially useful) for treating AMD. In preferred embodiments, a test compound is identified as useful (or as potentially useful) if it decreases expression of the αB-crystallin gene or gene product compared to expression in untreated or in placebo treated cells.

CONCLUSION

The present invention describes a previously unappreciated plasticity in an adult neural cell that can be extracted from even aged human RPE. Thus, the RPESC represents a type of 'neotonous' progenitor cell, which because of its early ontogeny and arrested development retains remarkable plasticity. Removing this cell from its native environment into culture releases it from dormancy and it actively proliferates to produce a variety of multi-lineage progeny. Because RPE cultures can be greatly expanded, they offer a long term source of RPESCs. In contrast to induced pluripotent stem cells, RPESC cell plasticity does not require exogenous gene transduction. Park et al., *Nature* (2008) 451:141-146; Nakagawa et al., *Nat. Biotechnol.* (2008) 26:101-111; Yu et al., *Science* (2007) 318:1917-1920. The ability to harvest RPE from patients indicates the possibility of generating patient-matched RPESC lines. In sum, the RPESC is a novel source of plastic adult human stem cells.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, GenBank® reference numbers, and protocols are cited throughout this application, the disclosures of which are incorporated herein by reference in their entireties for all purposes.

What is claimed is:

1. A method for treating a retinal disease or disorder selected from a group consisting of macular degeneration, age-related macular degeneration, retinitis pigmentosa, Leber's hereditary optic neuropathy and cone dystrophy, which method comprises administering, to the retina of a patient, an amount of retinal pigment epithelial stem cells (RPESCs) that is effective for treating the retinal disease or disorder, wherein the RPESCs (a) require growth factors in order to proliferate in serum-free culture conditions;

(b) express at least one marker selected from the group consisting of RPE65, Mitf, Cralbp, Otx2 and Bestrophin;

(c) express at least one marker selected from the group consisting of SSEA-4, Sox2, KLF4 and c-Myc;

(d) are self-renewing and capable of differentiating into a plurality of cell types, including retinal pigment epithelium (RPE) and mesodermal lineages; and (e) do not express any of the markers Chx10, Nanog and Oct4.

2. The method according to claim 1, wherein the retinal disease or disorder is macular degeneration or retinitis pigmentosa.

3. A method for treating a retinal disease or disorder selected from a group consisting of macular degeneration, age-related macular degeneration, retinitis pigmentosa, Leber's hereditary optic neuropathy and cone dystrophy, which method comprises (i) culturing one or more RPESCs isolated from the posterior RPE or descended from one or more RPESCs isolated from the posterior RPE of a mammal under conditions suitable for differentiation, wherein the RPESCs
- (a) require growth factors in order to proliferate in serum-free culture conditions;
- (b) express at least one marker selected from the group consisting of RPE65, Mitf, Cralbp, Otx2 and Bestrophin;
- (c) express at least one marker selected from the group consisting of SSEA-4, Sox2, KLF4 and c-Myc;
- (d) are self renewing and capable of differentiating into a plurality of cell types, including retinal pigment epithelium (RPE) and mesodermal lineages; and
- (e) do not express any of the markers Chx10, Nanog and Oct4; and (ii) administering an amount of the differentiated RPESCs to a retina of a patient that is effective for treating the retinal disease or disorder.

4. The method according to claim 3, in which the one or more RPESCs are cultured in the presence of at least one factor selected from the group consisting of nerve growth factor, glial cell-line derived growth factor, neurotrophin 3, neutrophin 4/5, neutrophin 6, ciliary neurotrophic factor, interleukin 6, interleukin 11, cardiotrophin 1, a growth factor hormone, hyaluronidase, chondroitinase ABC, fibroblast growth factor 2 (FGF2), fibroblast growth factor 8 (FGF8), retinoic acid (RA), N2 supplement, dexamethasone, beta-glycerophosphate, ascorbic acid, ascorbic acid-2-phosphate, BMP2, BMP4, activin, insulin, selenium, epidermal growth factor (EGF), and sonic hedgehog.

5. The method according to claim 4, in which the one or more factors include at least FGF2.

6. The method according to claim 3, in which the retinal disease or disorder is macular degeneration or retinitis pigmentosa.

7. The method according to claim 2 or 6, in which the macular degeneration is age-related macular degeneration.

8. The method according to claim 3, in which the RPESCs isolated from the retina of the patient are cultured under proliferative conditions.

9. The method according to claim 3, in which the RPESCs are differentiated to obtain retinal cells.

10. The method according to claim 3, in which the RPESCs are differentiated to obtain neural cells.

11. The method according to claim 3, in which the RPESCs are differentiated to obtain retinal pigment epithelial (RPE) cells.

12. The method according to claim 3, in which the RPESCs are RPESCs isolated from a retina of the patient.

* * * * *

UNITED STATES PATENT AND TRADEMARK OFFICE
CERTIFICATE OF CORRECTION

PATENT NO.        : 10,034,916 B2
APPLICATION NO.   : 13/915845
DATED             : July 31, 2018
INVENTOR(S)       : Temple et al.

Page 1 of 1

It is certified that error appears in the above-identified patent and that said Letters Patent is hereby corrected as shown below:

On the Title Page

Item (56), under OTHER PUBLICATIONS: delete "traficking" and insert -- trafficking -- therefor.

In the Claims

Column 85, Claim 4, Line 5: delete "neutrophin" and insert -- neurotrophin -- therefor.

Signed and Sealed this
Fourth Day of June, 2019

Andrei Iancu
*Director of the United States Patent and Trademark Office*

SEQUENCE LISTING

<160> NUMBER OF SEQ ID NOS: 132

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagaaggcct cagcacctac                                                 20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcactggca ggagaatttg g                                               21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cttgctgcag aagtgggtgg aggaa                                           25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgcagtgtg ggtttcgggc a                                               21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actctgagga ggaacaagaa                                                 20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggagacgtg gcacctctt                                                  19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctcaaggca cacctgcgaa                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagtgcctgg tcagttcatc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggatgtgga ggtagtgaga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggagatctc agtggctctt                                              20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcagactac gcaggaagg                                               19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcacgtcct ccaccgtg                                                18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catggacagt gtccgctcag                                              20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caggcagtcg cagttttca                                               19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcagctaca gcatgatgca g                                            21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctctggtag tgctgggaca tg                                           22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccatcagtt ccaacggaga ag                                           22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtggaattgg ttggtagaca ctg                                          23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccatgaccta tactcaggct tcagg                                          25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaagctccat atccctgggt ggaaag                                         26

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgctggagcc cttctttg                                                  18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcggacggtt cgtgtttg                                                  18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgatggcgt atatgaaccc                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcttgaacca aacctgaacc                                                20

<210> SEQ ID NO 25

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcgcatcatc agacctatgg                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccgaacagga caaactcaca                                                  20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggacgctgga ttagaaggca g                                                21

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttgtatgcat tgaaacctta cagg                                             24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccagagcatc tacgccaagt                                                  20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacgtcgtag agggagaagg                                                  20

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcatcatggt catcgctttc                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
catgaagatg ggaccgaagt                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gatgaatccg acacatgcag                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgttgcaaa caggccaata                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agctagagga gctggagaag                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
catgatgcca tccttggctg                                              20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
cggccaacaa gaagatgagt                                                     20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gccatggagt tcaagtcgtt                                                     20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cctttcttca tggagtcttt g                                                   21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
attgcagtgg cagttgtatt g                                                   21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttgccttgct gctctacctc                                                     20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaatgctttc tccgctctga                                                     20

<210> SEQ ID NO 43
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
atgtcagaag gggtggg                                                    17

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcagaaggct gtgttctca                                                  19

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggccagatct atgtactgga ataagcccga gc                                   32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggccctcgag ttaggaatgt gcttcatccc tg                                   32

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaatgtgat gtatgatagc c                                               21

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgatttcggt ttgttctgg                                                  19

<210> SEQ ID NO 49
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 49
ttgctgcaaa gctgaaaatg                                              20

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcagcattct gttatttgt ttgac                                         25

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tgcttccctg agacccagtt                                              20

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatcacttct ttcctttgca tcaag                                        25

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctcgtctcgt ccccagactc at                                           22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agtttctccc gctcactggc                                              20

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 55
catgctagtt tgatacctga gacg                                      24

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctgaggttaa agaggaaacg aaaag                                     25

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tctggccttc cactctcagt                                           20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gactggcggg gtgtaagtaa                                           20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cggaggagac aatggagaag                                           20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gacgcccgtg tattcgtact                                           20

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 61
tgaatctgat gaactggtca ctga                                         24

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggtgatgtcc tcgtctgtag c                                            21

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agacactggt gctaagggag ag                                           22

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gaccagcaac accatctgcg                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtgcaggaga agtgccagct                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gagggtggcg gtctcatagt                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 67
ctcctattga cccagaaagc                                           20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtagagctga gtcttctcag                                           20

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cccCttcatt gacctcaact aca                                       23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttgctgatga tcttgaggct gt                                        22

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tccctgtcca agtccaacag caat                                      24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaattcggtt tcgcacacgt accc                                      24

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggtgctgggc ttgctttt                                                18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cgtggctgga gttggtgtta                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcactgtaca ccaaagcacg                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
taggtgggtg gacagtagga                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agcgaactgg acacacatac                                              20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tctagactgg gcatcgcag                                               19

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctcctctact tcagcctctt                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttcatcaaa gtcctgtggg                                                    20

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atacgacact gtcccggccc taaa                                               24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttctcctctg tccagcctgt tctc                                               24

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
caggagaccg ggtccatc                                                      18

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgaacttgat tctgagcacg                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgcgtgacat taaggagaag                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgaaggtagt ttcgtggatg                                          20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccgcaccacc aactttttca t                                        21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tggacagggt ctctacctgc                                          20

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tcaagactga ctcacagcaa cccc                                     24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ctttgtcctg aaccgtggtg gtag                                     24

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atcccctaag ctccat                                              16

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aggagggagt taggtg                                                     16

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cttcttcagg tcccaggtcc                                                 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ctctgtcagg tacctgttgg                                                 20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gagtacaccg ccgaggagat tg                                              22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcggatatac tgggtgcact gg                                              22

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tcctgcactc cctgtcagag                                                 20

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccaagagcag cccatcaaag g                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99 ttctcccttta agcaatcgcc c                                             21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aagcctttgc agccctcaca g                                              21

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ctggctatgg tcacagagag                                                20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acaggtagtt gggtcggttc                                                20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
atgttcgcct gggagattcg                                                20

<210> SEQ ID NO 104

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcaagtgctt ccgcaaactg                                                 20

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccaaagtggt ggacaagatt gcc                                             23

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gggataggaa ggacgctcaa agac                                            24

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
caatgcgggg aggagaagtc                                                 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ctctggacca aactgtggcg                                                 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cctcggatct ctggtcaagt                                                 20

<210> SEQ ID NO 110
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tacagagccg gcagtcatac                                              20

<210> SEQ ID NO 111
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
actaggccct acacac                                                  16

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112 ttttttgac agtccgc                                                  17

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aggacggctc tctgaagaa                                               19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ttgaccgagt tgaaggcgaa                                              20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tcagcgatga gcacggcata                                              20

<210> SEQ ID NO 116
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 116
cactctttcc gcacgacatc                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
ggagagtcgc ttagaggtgc                                               20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
tcaggaaagc caagagaagc                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
agcgaaccag tatcgagaac                                               20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
ttacagaacc acactcggac                                               20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
agctacagca tgatgcagga                                               20

<210> SEQ ID NO 122
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 122
ggtcatggag ttgtactgca                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgaacctcag ctacaaacag                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tggtggtagg aagagtaaag                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
actctgagga ggaacaagaa                                                    20

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tggagacgtg gcacctctt                                                     19

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tctcaaggca cacctgcgaa                                                    20

<210> SEQ ID NO 128
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 128
tagtgcctgg tcagttcatc                                              20

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aggcggtgga gttcaccttt aaga                                         24

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
agcttgcatt ccttggcatg atgg                                         24

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccccttcatt gacctcaact aca                                          23

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ttgctgatga tcttgaggct gt                                           22
```